(12) United States Patent
Farrell et al.

(10) Patent No.: US 9,470,618 B2
(45) Date of Patent: Oct. 18, 2016

(54) SHEATH FLUID SYSTEMS AND METHODS FOR PARTICLE ANALYSIS IN BLOOD SAMPLES

(71) Applicant: IRIS International, Inc., Chatsworth, CA (US)

(72) Inventors: Gregory A. Farrell, Ridgewood, NJ (US); Bart J. Wanders, Trabuco Canyon, CA (US); Thomas H. Adams, Encinitas, CA (US); Warren Groner, Somers, NY (US); Xiaodong Zhao, San Diego, CA (US)

(73) Assignee: IRIS International, Inc., Chatsworth, CA (US)

(*) Notice: Subject to any disclaimer, the term of this patent is extended or adjusted under 35 U.S.C. 154(b) by 0 days.

(21) Appl. No.: 15/064,129

(22) Filed: Mar. 8, 2016

(65) Prior Publication Data

US 2016/0187246 A1 Jun. 30, 2016

Related U.S. Application Data

(62) Division of application No. 14/215,834, filed on Mar. 17, 2014, now Pat. No. 9,316,635.

(60) Provisional application No. 61/799,152, filed on Mar. 15, 2013.

(51) Int. Cl.
*G01N 33/48* (2006.01)
*G01B 11/00* (2006.01)
(Continued)

(52) U.S. Cl.
CPC ...... *G01N 15/1436* (2013.01); *G01N 15/1404* (2013.01); *G01N 15/147* (2013.01); *G01N 15/1434* (2013.01); *G01N 15/1463* (2013.01); *G01N 15/1468* (2013.01); *G01N 15/1475* (2013.01); *G01N 33/5091* (2013.01);
(Continued)

(58) Field of Classification Search
CPC ............ G01N 33/48; G01N 15/1436; G01N 15/1468; G01N 15/1404; G01N 15/1434; G01N 15/147; G01B 11/00
USPC .................................................. 356/39, 390
See application file for complete search history.

(56) References Cited

U.S. PATENT DOCUMENTS 3,822,095 A 7/1974 Hirschfield
4,338,024 A 7/1982 Bolz et al.
(Continued)

FOREIGN PATENT DOCUMENTS

CA 2349995 A1 12/2001
CN 1265196 A 8/2000
(Continued)

OTHER PUBLICATIONS

Harned, et al. 1946, vol. 68:966-967.
(Continued)

*Primary Examiner* — Roy M Punnoose
(74) *Attorney, Agent, or Firm* — Kilpatrick Townsend & Stockton LLP

(57) ABSTRACT

Aspects and embodiments of the instant disclosure provide a particle and/or intracellular organelle alignment agent for a particle analyzer used to analyze particles contained in a sample. An exemplary particle and/or intracellular organelle alignment agent includes an aqueous solution, a viscosity modifier, and/or a buffer.

21 Claims, 22 Drawing Sheets

(51) Int. Cl.
*G01N 15/14* (2006.01)
*G01N 33/50* (2006.01)
*G01N 15/00* (2006.01)
*G01N 15/10* (2006.01)
*G01N 21/05* (2006.01)

(52) U.S. Cl.
CPC . *G01N2015/008* (2013.01); *G01N 2015/0065* (2013.01); *G01N 2015/0073* (2013.01); *G01N 2015/0084* (2013.01); *G01N 2015/1006* (2013.01); *G01N 2015/1037* (2013.01); *G01N 2015/1409* (2013.01); *G01N 2015/1411* (2013.01); *G01N 2015/1413* (2013.01); *G01N 2015/1452* (2013.01); *G01N 2015/1486* (2013.01); *G01N 2021/058* (2013.01)

(56) References Cited

U.S. PATENT DOCUMENTS

| | | | |
|---|---|---|---|
| 4,428,669 A | 1/1984 | Bessis | |
| 4,732,479 A | 3/1988 | Tanaka et al. | |
| 5,159,403 A * | 10/1992 | Kosaka | G01N 15/1459 250/201.2 |
| 5,308,526 A | 5/1994 | Dias | |
| 5,412,466 A * | 5/1995 | Ogino | G01N 15/1404 356/246 |
| 5,436,978 A | 7/1995 | Kasdan | |
| 5,457,526 A | 10/1995 | Kosaka | |
| 5,585,246 A | 12/1996 | Dubrow | |
| 5,633,503 A | 5/1997 | Kosaka | |
| 5,690,895 A * | 11/1997 | Matsumoto | G01N 15/1404 356/246 |
| 5,812,419 A | 9/1998 | Chupp et al. | |
| 5,822,447 A | 10/1998 | Kasdan | |
| 6,184,976 B1 | 2/2001 | Park et al. | |
| 6,184,978 B1 | 2/2001 | Kasdan et al. | |
| 6,424,415 B1 | 7/2002 | Kasdan et al. | |
| 6,441,894 B1 | 8/2002 | Manian et al. | |
| 6,590,646 B2 | 7/2003 | Kasdan et al. | |
| 6,632,676 B1 | 10/2003 | Crews et al. | |
| 6,825,926 B2 | 11/2004 | Turner et al. | |
| 7,822,276 B2 | 10/2010 | Turner et al. | |
| 7,824,916 B2 | 11/2010 | Fujimoto | |
| 8,445,284 B2 | 5/2013 | Lapen et al. | |
| 9,279,750 B2 | 3/2016 | Cremins | |
| 9,316,635 B2 * | 4/2016 | Farrell | G01N 33/5091 |
| 9,322,752 B2 * | 4/2016 | Wanders | G01N 33/5094 |
| 2004/0070757 A1 | 4/2004 | Moore et al. | |
| 2004/0180444 A1 | 9/2004 | Rannikko et al. | |
| 2005/0180885 A1* | 8/2005 | Tateishi | G01N 15/1404 422/68.1 |
| 2006/0148028 A1 | 7/2006 | Noda et al. | |
| 2007/0020721 A1 | 1/2007 | Yoshida | |
| 2007/0111276 A1 | 5/2007 | Lefevre et al. | |
| 2008/0019584 A1 | 1/2008 | Lindberg et al. | |
| 2008/0138852 A1 | 6/2008 | Winkelman et al. | |
| 2008/0283722 A1 | 11/2008 | Uchiyama et al. | |
| 2009/0011430 A1 | 1/2009 | Ateya et al. | |
| 2009/0269799 A1 | 10/2009 | Winkelman et al. | |
| 2010/0178666 A1 | 7/2010 | Leshansky et al. | |
| 2010/0284602 A1 | 11/2010 | Winkelman et al. | |
| 2011/0014645 A1 | 1/2011 | Winkelman et al. | |
| 2011/0070606 A1 | 3/2011 | Winkelman et al. | |
| 2011/0128545 A1 | 6/2011 | Cox | |
| 2012/0035061 A1 | 2/2012 | Bransky et al. | |
| 2012/0301883 A1 | 11/2012 | Pagano et al. | |
| 2012/0322099 A1 | 12/2012 | Lapen et al. | |
| 2013/0070249 A1 | 3/2013 | Choi et al. | |
| 2014/0273067 A1* | 9/2014 | Wanders | G01N 33/5094 435/29 |
| 2014/0273068 A1* | 9/2014 | Wanders | G01N 33/5094 435/29 |
| 2014/0315238 A1* | 10/2014 | Farrell | G01N 15/1404 435/29 |
| 2014/0329265 A1* | 11/2014 | Wanders | G01N 15/1468 435/29 |

FOREIGN PATENT DOCUMENTS

| | | |
|---|---|---|
| CN | 101013080 A | 8/2007 |
| CN | 102998437 A | 3/2013 |
| EP | 0 286 088 A2 | 10/1988 |
| EP | 0 468 100 A1 | 1/1992 |
| EP | 0 486 747 A2 | 5/1992 |
| EP | 0 556 971 A2 | 8/1993 |
| EP | 0 656 540 A2 | 6/1995 |
| EP | 1264205 A2 | 12/2002 |
| EP | 1761817 A1 | 3/2007 |
| EP | 2028264 A1 | 2/2009 |
| EP | 2030062 A1 | 3/2009 |
| GB | 1 471 976 A | 4/1977 |
| GB | 1 557 691 A | 12/1979 |
| GB | 2121976 A | 1/1984 |
| JP | 2003-005086 A | 1/2003 |
| WO | 99-05504 A2 | 2/1999 |
| WO | 00-11449 A1 | 3/2000 |
| WO | 01-48455 | 7/2001 |

OTHER PUBLICATIONS

Wu et al. Biomedical Microdevices, 2005, 7(1):13-20.
International Search Report and Written Opinion for Application No. PCT-US2014-030942 mailed Oct. 14, 2014, all pages.
International Preliminary Report on Patentability for Application No. PCT-US2014-030942 mailed Sep. 24, 2015, all pages.
Kachel et al, Uniform Lateral Orientation, Cause by Flow Forces, of Flat Particles in Flow-Through Systems, Journal of Histochemistry and Cytochemistry, Jan. 1, 1977, pp. 774-780, vol. 25, No. 7, Histochemical Society, New York, NY, US.
Cubaud, et al. "High-viscosity fluid threads in weakly diffusive microfluidic systems," New Journal of Physics, Institute of Physics Publishing, vol. 11 No. 7. Jul. 31, 2009. 14 pages.
Zhigang, et al. "Rapid Mixing Using Two-Phase Hydraulic Focusing in Microchannels," Biomedical Microdevices, Kluwer Academic Publishers, BO. vol. 7, No. 1. Mar. 1, 2005. 15 pages.
International Search Report and Written Opinion of PCT-US2014-030850 mailed on Jun. 27, 2014, 22 pages.
International Preliminary Report on Patentability of PCT-US2014-030850 mailed on Sep. 24, 2015, all pages.
International Search Report and Written Opinion of PCT-US2014-030851 mailed on Jul. 16, 2014, all pages.
International Preliminary Report on Patentability of PCT-US2014-030851 mailed on Sep. 24, 2015, all pages.
International Preliminary Report on Patentability of PCT-US2014-030928 mailed on Sep. 24, 2015, all pages.
International Search Report and Written Opinion of of PCT-US2014-030928 mailed on Jun. 18, 2014, all pages.
Anonymous, "Coulter VCS Reticulocyte method", Internet Citation, Oct. 25, 1996, pp. 1-2, retrieved from: www.cyto.purdue.edu-cdroms-cyto2-6-coulter-ss600126.html
Wietzorrek, et al. "A New Multiparameter Flow Cytometer: Optical and Electrical Cell Analysis in Combination With Video Microscopy in Flow", Apr. 1, 1999 retrieved from: http:-- onlinelibrary.wiley.com-store , 11 pages.

* cited by examiner

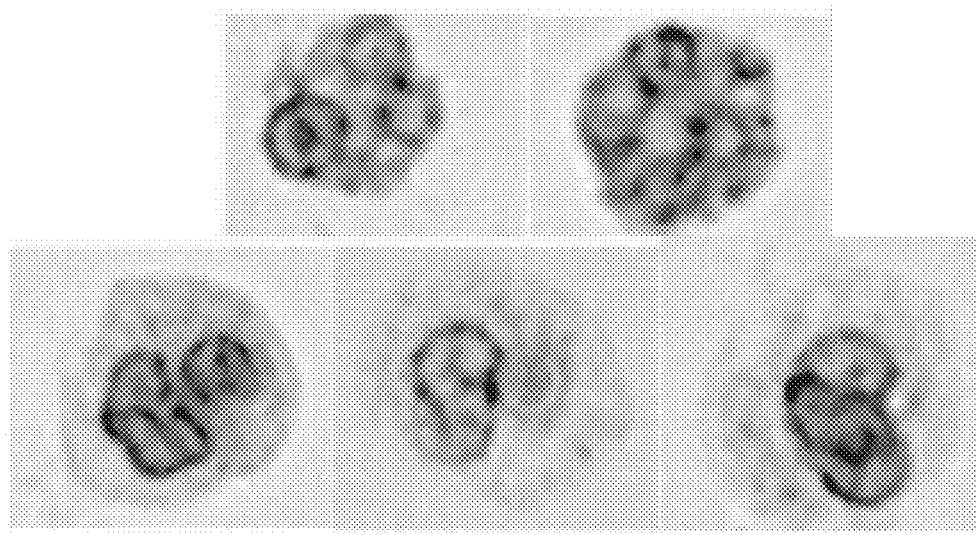
(upper panel)
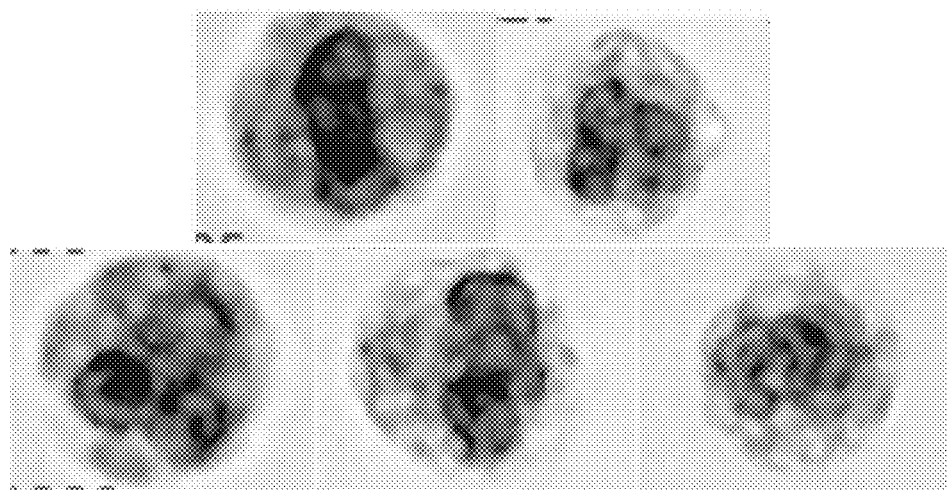
FIG.4H (lower panel)

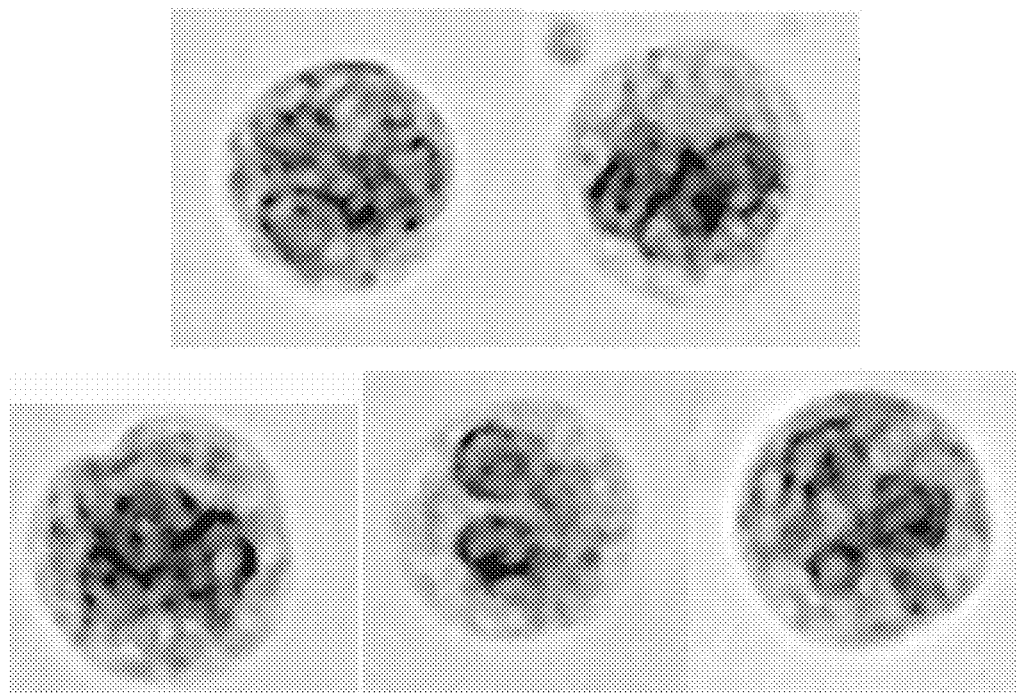
(upper panel)
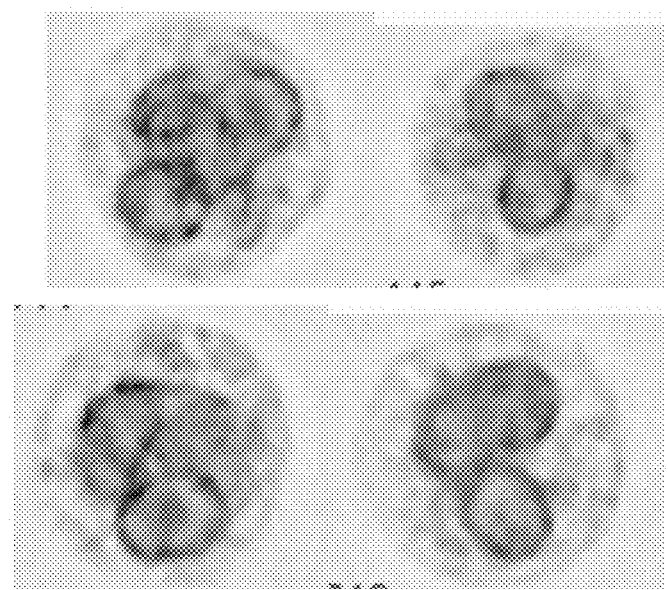
FIG.4I (lower panel)

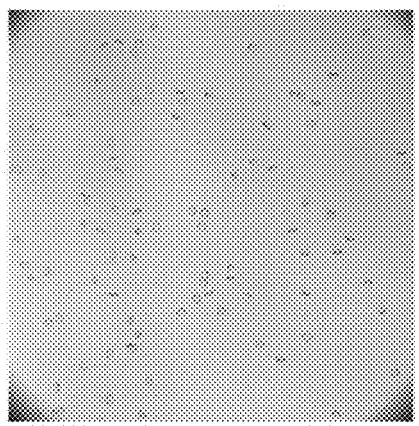
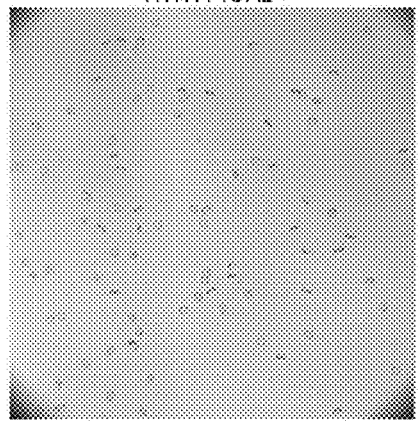
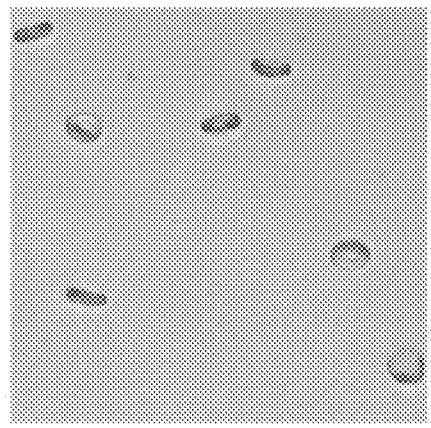
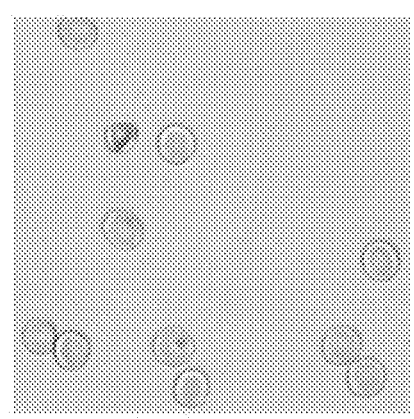
FIG.4P　　　　　　FIG.4Q

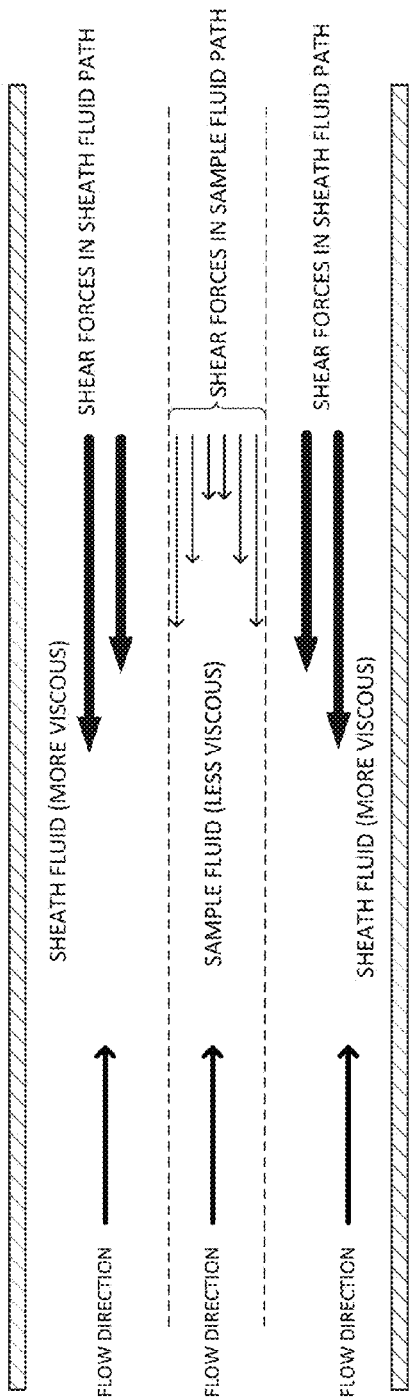
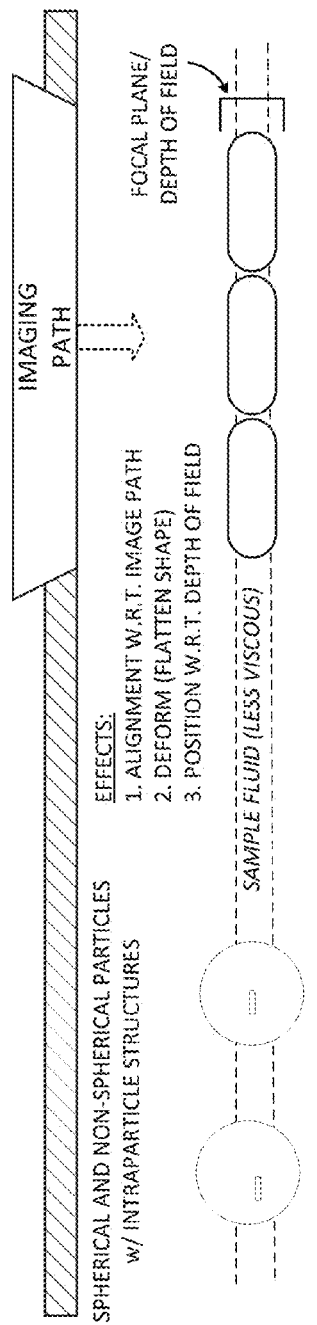
FIG. 5A
FIG. 5B

SHEATH FLUID SYSTEMS AND METHODS FOR PARTICLE ANALYSIS IN BLOOD SAMPLES

CROSS-REFERENCES TO RELATED APPLICATIONS

This application is a divisional of U.S. patent application Ser. No. 14/215,834, which was filed on Mar. 17, 2014, which is a non-provisional of, and claims the benefit of priority to, U.S. Provisional Patent Application No. 61/799,152 filed Mar. 15, 2013, the content of each of which is incorporated herein by reference. This application is also related to U.S. patent application Ser. Nos. 14/216,811, 14/216,533, 14/217,034, and 14/216,339 and International Patent Application Nos. PCT/US14/30928, PCT/US14/30902, and PCT/US14/30851, all filed Mar. 17, 2014. The content of each of these filings is incorporated herein by reference.

BACKGROUND OF THE INVENTION

This disclosure relates to the field of apparatus, systems, compositions, and methods for analysis of particles, including imaging of particles in fluid samples, using wholly or partly automated devices to discriminate and quantify particles such as blood cells in the sample. The present disclosure also relates to a particle and/or intracellular organelle alignment liquid (PIOAL) useful for analyzing particles in a sample from a subject, methods for producing the liquid, and methods for using the liquid to detect and analyze particles. Compositions, systems, devices and methods useful for conducting image-based biological fluid sample analysis are also disclosed. The compositions, systems, devices, and methods of the present disclosure are also useful for detecting, counting and characterizing particles in biological fluids such as red blood cells, reticulocytes, nucleated red blood cells, platelets, and for image and morphologically-based white blood cell differential counting, categorization, subcategorization, characterization and/or analysis.

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PLTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

Although such currently known particle analysis systems and methods, along with related medical diagnostic techniques, can provide real benefits to doctors, clinicians, and patients, still further improvements are desirable. For example, there is a continuing need for improved methods and compositions useful for particle and/or intracellular organelle alignment when performing image-based sample analysis using automated systems. Embodiments of the present invention provide solutions for at least some of these outstanding needs.

BRIEF SUMMARY OF THE INVENTION

Embodiments of the present invention relate to apparatus, systems, compositions, and methods for analyzing a prepared sample containing particles. In some aspects the system comprises an analyzer which may be a visual analyzer. In some aspects, the apparatus contains a visual analyzer and a processor. In one aspect, this disclosure relates to an automated particle imaging system in which a liquid sample containing particles of interest is caused to flow through a flowcell having a viewport through which a high optical resolution imaging device captures an image. In some aspects the high optical resolution imaging device comprises a camera such as a digital camera. In one aspect the high optical resolution imaging device comprises an objective lens.

The flowcell is coupled to a source of sample fluid, such as a prepared sample, and to a source of particle and/or intracellular organelle alignment liquid (PIOAL). The system permits capture of focused images of particles in a sample in flow. In some embodiments the images can be used in automated, high throughput processes for categorizing and subcategorizing particles. An exemplary visual analyzer may include a processor to facilitate automated analysis of the images. In some cases, the visual analyzer can be used in methods of this disclosure to provide automated image-based WBC differential counting or other blood sample particle analysis protocols. In some cases, the methods of this disclosure relate to automated identification of morphological abnormalities for determining, diagnosing, prognosing, predicting, and/or supporting a diagnosis of whether a subject is healthy or has a disease, condition, abnormality and/or infection and for monitoring whether a subject is responsive or non-responsive to treatment.

Embodiments of the present invention provide systems, methods, and sheath fluid compositions useful for particle and/or intracellular organelle alignment in cells treated with particle contrast agent compositions. Such techniques overcome certain difficulties associated with conventional sheath fluids used in flow cytometry that may suffer from the disadvantages of maintaining cell morphology and/or not providing for the capture of optimized images which permit determination of one or more blood components.

In certain embodiments, a viscosity difference and/or speed difference between a ribbon-shaped sample stream and a sheath fluid and/or a thickness of the ribbon-shaped sample stream, for example in combination with a geometric focusing effect provided by a narrowing flowpath transition zone, can introduce shear forces to act on the particles while in flow thereby causing the particles to align or remain in alignment throughout an imaging process in a visual analyzer. In some embodiments the sample will be contrast enhanced. In some embodiments the sheath fluid may comprise up to 100% of a viscosity agent. In another embodiment, the sheath fluid has up to 60% v/v of a viscosity agent. Depending on the types of viscosity agent used, in some embodiments the sheath fluid may comprise a viscosity agent that is commercially available in dry form at a concentration of about 5 to 7%, or more specifically at 6.5% (w/v).

In other embodiments, this disclosure relates to a sheath fluid that can be used in image based analysis of particles in samples such as cells and other particle features in other biological fluids such as cerebrospinal fluid and effusions associated with particular conditions. Cell category and/or subcategory counts as described for use in blood samples in this disclosure as nonlimiting examples of the sort of samples that may be analyzed. In some embodiments, cells present in samples may also include bacterial or fungal cells as well as white blood cells, red blood cells or platelets. In some embodiments, particle suspensions obtained from tissues or aspirates may be analyzed.

In some embodiments a stream of sample fluid can be injected through a cannula with a flattened opening to establish a flowpath with a considerable width. The sheath fluid can be introduced into the flowcell and carries the sample fluid along through the imaging area, then toward a discharge. A sheath fluid has a different viscosity, e.g., higher, than the sample fluid, and, optionally, a different flow rate at the point of injection to the ribbon-shaped sample stream results in the sample fluid flattening into a thin ribbon shape. The thin ribbon of sample fluid is carried along with the sheath fluid, through a narrowing flowpath transition zone, to pass in front of a viewing port where a high optical resolution imaging device and a light source are arranged to view the ribbon-shaped sample stream.

In one embodiment, the viscosity of the sheath fluid can be higher than the viscosity of the sample. The viscosity of the sheath fluid, the viscosity of the sample material, the flow rate of the sheath fluid and the flow rate of the sample material are coordinated, for example in combination with a ribbon compression effect provided by a narrowing transition zone, to provide the flow in a ribbon-shaped sample stream with predetermined dimensional characteristics, such as an advantageous ribbon-shaped sample stream thickness. Maintaining an advantageous ribbon-shaped sample stream thickness provides, as an example, a high percentage of in-focus cells or in-focus cellular components.

Embodiments of the instant disclosure are based at least in part on the discovery that the addition of a suitable amount of a viscosity agent in the sheath fluid significantly improves particle/cell alignment in a flowcell, for example in a flowcell having a narrowing transition zone, and increases in-focus intracellular contents of cells, resulting in higher quality images of cells in flow compared to use of a non viscosity-modified conventional sheath fluid used in flow cytometry. The addition of the viscosity agent increases the shear forces on elongate or nonspherical particles or cells like red blood cells (RBCs) which then aligns the cells in a plane substantially parallel to the flow direction, which results in image optimization. For cells like white blood cells (WBCs), this also results in positioning, repositioning, and/or better-positioning of intracellular structures, organelles or lobes substantially parallel to the direction of flow. For example, the white blood cells can be compressible or deformable in response to the shear forces conferred by the viscosity agent or differential, thus leading to particle elongation or compression and alignment under shear.

Alignment of particles that are smaller in diameter than the flow stream may be obtained by increasing the viscosity of the sheath fluid. This results in improved alignment of those particles in a plane substantially parallel to the direction of the flow.

The ribbon-shaped sample stream thickness can be affected by the relative viscosities and flow rates of the sample fluid and the sheath fluid, for example in combination with the geometry of the narrowing transition zone of the flowcell. The feed source of the sample and/or the feed source of the sheath fluid, for example comprising precision displacement pumps, can be configured to provide the sample and/or the sheath fluid at stable flow rates for optimizing the dimensions of the ribbon-shaped sample stream, namely as a thin ribbon at least as wide as the field of view of the imaging device.

An exemplary sheath fluid embodiment is used in a flowcell for particle analysis. A sample is enveloped in the stream of the sheath fluid and passed through the flowcell of the analyzer device. Then information from the sample when passing through the detection area is collected, enabling an analyzer to analyze particles/cells contained in the sample. The use of the sheath fluid on such an analyzer allows accurate categorization and subcategorization and counting of cells and/or particles contained in samples.

As used herein, sheath fluid is useful in obtaining information relating to following cells and/or particles related thereto: including for example; neutrophil, lymphocyte, monocyte, eosinophil, basophil, platelet, reticulocyte, nucleated RBC, blast, promyelocyte, myelocyte, and/or a metamyelocyte.

The present disclosure provides novel compositions and methods of use thereof for conducting particle analysis. In particular, the present disclosure relates to a particle and/or intracellular organelle alignment liquid (PIOAL) used in a analyzer for analyzing particles in a sample. The terms sheath fluid and PIOAL can be used interchangeably throughout this disclosure. The present disclosure further provides methods for producing the PIOAL and methods for using the PIOAL to analyze particles. The PIOAL of this invention is useful, as an example, in methods for automated categorization and subcategorization of particles in a sample.

In one aspect, embodiments of the present invention encompass methods for imaging a plurality of particles using a particle analysis system. The system can be configured for combined viscosity and geometric hydrofocusing. The particles can be included in a blood fluid sample having a sample fluid viscosity. Exemplary methods can include flowing a sheath fluid along a flowpath of a flowcell, and the sheath fluid can have a sheath fluid viscosity that differs from the sample fluid viscosity by a viscosity difference in a predetermined viscosity difference range. Methods can also include injecting the blood fluid sample into the flowing sheath fluid within the flowcell so as to provide a sample fluid stream enveloped by the sheath fluid. Further, methods can include flowing the sample fluid stream and the sheath fluid through a reduction in flowpath size toward an imaging site, such that a viscosity hydrofocusing effect induced by an interaction between the sheath fluid and the sample fluid stream associated with the viscosity difference, in combination with a geometric hydrofocusing effect induced by an interaction between the sheath fluid and the sample fluid stream associated with the reduction in flowpath size, is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. What is more, methods may include imaging the plurality of particles at the imaging site. In some cases, the sheath fluid has an index of refraction n=1.3330. In some cases, the sheath fluid has an index of refraction that is the same as the index of refraction of water. In some cases, the interaction between the sheath fluid and the sample fluid stream associated with the reduction in flowpath size contributes to providing the target imaging state by producing shear forces along the interfaces of the sample and sheath fluid streams. In some cases, the target imaging state includes a target orientation of one or more target particles in the flow relative to a focal plane of an imaging device used to acquire images at the imaging site. According to some embodiments, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to the focal plane at the imaging site. In some cases, the target alignment corresponds to a target intraparticle structure alignment relative to the focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target orientation of one or more target intraparticle structures in the flow relative to a focal plane of an imaging device used to acquire images at the imaging site. In some cases, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to the focal plane at the imaging site. In some cases, the target alignment corresponds to a target intraparticle structure alignment relative to the focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target deformation of one or more target particles or of one or more target intraparticle structures.

According to some embodiments, the process of injecting the blood fluid sample is performed by directing a stream of the blood fluid sample through a sample injection tube with a sample fluid velocity. The injection tube can have a port within the flowpath. The port can define a width, a thickness, and a flow axis extending along the flowpath. The width can be being greater than the thickness so that the sample stream has opposed major surfaces transverse to the imaging path adjacent the imaging site. In some cases, the sheath fluid flowing along the flowpath of the flowcell extends along the major surfaces of the sample stream and has a sheath fluid velocity different than the sample fluid velocity. In some cases, an interaction between the sheath fluid and the sample fluid associated with the differing velocities, in combination with the interaction between the sheath fluid and the sample fluid associated with the differing viscosities, provides the target imaging state. According to some embodiments, the plurality of particles can include a red blood cell, a white blood cell, and/or a platelet. According to some embodiments, the plurality of particles can include a cell having an intraparticle structure. In some cases, an intraparticle structure can be an intracellular structure, an organelle, or a lobe.

In some embodiments, the sheath fluid has a viscosity between 1 and 10 centipoise (cP). In some cases, the predetermined viscosity difference has an absolute value within a range from about 0.1 to about 10 centipoise (cP). In some cases, the predetermined viscosity difference has an absolute value within a range from about 1.0 to about 9.0 centipoise (cP). In some cases, the predetermined viscosity difference has an absolute value within a range from about 1.0 to about 5.0 centipoise (cP). In some cases, predetermined viscosity difference has an absolute value of about 3.0 centipoise (cP). In some cases, the viscosity agent of the sheath fluid includes glycerol, glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes glycerol and polyvinylpyrrolidone (PVP). In some cases, the viscosity agent of the sheath fluid includes glycerol at a concentration of 5% (v/v) and glycerol and polyvinylpyrrolidone (PVP) at a concentration of 1% (w/v). In some cases, the viscosity agent of the sheath fluid includes glycerol present at a final concentration between about 3 to about 30% (v/v) under operating conditions. In some cases, the viscosity agent of the sheath fluid includes glycerol present at a final concentration of about 30% (v/v) under operating conditions. In some cases, the viscosity agent of the sheath fluid includes glycerol present at a final concentration of about 6.5% v/v under operating conditions. In some cases, the viscosity agent of the sheath fluid includes glycerol present at a final concentration of about 5% (v/v) and polyvinylpyrrolidone (PVP) present at a concentration of about 1% (w/v) under operating conditions.

According to some embodiments, the blood fluid sample at the imaging site has a linear velocity within a range from 20 to 200 mm/second. In some cases, the blood fluid sample at the imaging site has a linear velocity within a range from 50 to 150 mm/second. In some cases, the blood fluid sample has a sample stream thickness of up to 7 µm and a sample stream width within a range from 500 to 3000 µm at the imaging site. In some cases, the blood fluid sample has sample stream thickness within a range from 2 to 4 µm and a sample stream width within a range from 1000 to 2000 µm at the imaging site. In some cases, the plurality of particles includes a set of non-spherical particles, the blood fluid sample has a direction of flow at the imaging site, and more than 75% of the set of non-spherical particles are aligned substantially in a plane parallel to the direction of flow such a major surface of each aligned non-spherical particle is parallel to the plane parallel to the direction of flow. In some cases, the plurality of particles includes a set of non-spherical particles, the blood fluid sample has a direction of flow at the imaging site, and at least 90% of the set of non-spherical particles are aligned within 20 degrees from a plane substantially parallel to the direction of flow. In some cases, the plurality of particles includes intraparticle structures, the blood fluid sample has a direction of flow at the imaging site, and at least 92% of the intraparticle structures are substantially parallel to the direction of flow.

In another aspect, embodiments of the present invention encompass systems for imaging a plurality of particles in a blood fluid sample having a sample fluid viscosity. The system can be configured for use with a sheath fluid having a sheath fluid viscosity that differs from the sample fluid viscosity by a viscosity difference in a predetermined viscosity difference range. Exemplary systems can include a flowcell having a flowpath and a sample fluid injection tube, the flowpath having a reduction in flowpath size, a sheath fluid input in fluid communication with the flowpath of the flowcell so as to transmit a flow of the sheath fluid along the flowpath of the flowcell, and a blood fluid sample input in fluid communication with the injection tube of the flowcell so as to inject a flow of the blood fluid sample into the flowing sheath fluid within the flowcell, such that as the sheath fluid and the sample fluid flow through the reduction in flowpath size and toward an imaging site, a viscosity hydrofocusing effect induced by an interaction between the sheath fluid and the sample fluid associated with the viscosity difference, in combination with a geometric hydrofocusing effect induced by an interaction between the sheath fluid and the sample fluid associated with the reduction in flowpath size, provides a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. Systems can further include an imaging device that images the plurality of particles at the imaging site.

According to some embodiments, the target imaging state corresponds to a target orientation of one or more target particles in the flow relative to a focal plane of an imaging device used to acquire images at the imaging site. In some cases, the plurality of particles includes a member selected from the group consisting of a red blood cell, a white blood cell, and a platelet. In some cases, the plurality of particles includes a cell having an intraparticle structure. An intracellular structure can be an intracellular structure, an organelle, or a lobe. In some cases, the predetermined viscosity difference has an absolute value within a range from about 0.1 to about 10 centipoise (cP). In some cases, the viscosity agent of the sheath fluid includes glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes glycerol and polyvinylpyrrolidone (PVP). In some cases, the viscosity agent of the sheath fluid includes glycerol at a concentration of 5% (v/v) and glycerol and polyvinylpyrrolidone (PVP) at a concentration of 1% (w/v).

According to some embodiments, the plurality of particles includes a set of non-spherical particles, the blood fluid sample has a direction of flow at the imaging site, and at least 90% of the set of non-spherical particles are aligned within 20 degrees from a plane substantially parallel to the direction of flow. In some cases, the target orientation corresponds to a target particle orientation relative to a focal plane at the imaging site. A particle may be a red blood cell, an white blood cell, or a platelet, in some embodiments. In some cases, the target orientation corresponds to a target intraparticle structure orientation relative to a focal plane at the imaging site. (e.g. intraparticle structure can be an intracellular structure, an organelle, or a lobe). In some cases, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to a focal plane at the imaging site. In some cases, the target alignment corresponds to a target intraparticle structure alignment relative to a focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target deformation at the imaging site.

According to some embodiments, a blood fluid sample source can be configured to provide the blood fluid sample a sample fluid velocity into the flowing sheath fluid, such that the sheath fluid has a sheath fluid velocity that is different from the sample fluid velocity. In some cases, an interaction between the sheath fluid and the sample fluid associated with the differing velocities, in combination with the interaction between the sheath fluid and the sample fluid associated with the differing viscosities, provides the target imaging state.

According to some embodiments, the flowpath of the flowcell includes a zone with a change in flowpath size, and an interaction between the sheath fluid and the sample fluid associated with the change in flowpath size, in combination with the interaction between the sheath fluid and the sample fluid associated with the differing viscosities, provides the target imaging state. In some cases, the interaction between the sheath fluid and the sample fluid associated with the change in flowpath size contributes to providing the target imaging state by producing a lateral fluid compression force. In some cases, the plurality of particles includes a red blood cell, a white blood cell, and/or a platelet. In some cases, the plurality of particles includes a cell having an intraparticle structure, and the structure can be an intracellular structure, an organelle, or a lobe.

According to some embodiments, the predetermined viscosity difference has an absolute value within a range from about 0.1 to about 10 centipoise (cP). In some cases, the predetermined viscosity difference has an absolute value within a range from about 1.0 to about 9.0 centipoise (cP). In some cases, the predetermined viscosity difference has an absolute value within a range from about 1.0 to about 5.0 centipoise (cP). In some cases, the predetermined viscosity difference has an absolute value of about 3.0 centipoise (cP). In some cases, the sheath fluid includes a viscosity agent which can include glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the sheath fluid comprises glycerol at a concentration between about 1 to about 50% (v/v).

According to some embodiments, the blood fluid sample at the imaging site has a linear velocity within a range from 20 to 200 mm/second. In some cases, the blood fluid sample at the imaging site has a linear velocity within a range from 50 to 150 mm/second. In some cases, the blood fluid sample has a sample stream thickness of up to 7 μm and a sample stream width of over 500 μm at the imaging site. In some cases, the blood fluid sample has a sample stream thickness within a range from 2 to 4 μm and a sample stream width within a range from 1000 to 2000 μm at the imaging site. In some cases, the plurality of particles includes a set of non-spherical particles, the blood fluid sample has a direction of flow at the imaging site, and at least 90% of the set of non-spherical particles are aligned and/or positioned substantially in a plane parallel to the direction of flow. In some cases, the plurality of particles includes a set of non-spherical particles, the blood fluid sample has a direction of flow at the imaging site, and at least 95% of the set of non-spherical particles are aligned within 20 degrees from a plane substantially parallel to the direction of flow. In some cases, the plurality of particles include intraparticle structures, the blood fluid sample has a direction of flow at the imaging site, and at least 92% of the intraparticle structures are substantially parallel to the direction of flow.

In another aspect, embodiments of the present invention encompass a particle and intracellular organelle alignment liquid (PIOAL) for use in a combined viscosity and geometric hydrofocusing analyzer. The PIOAL can direct flow of a blood sample fluid of a given viscosity that is injected into a narrowing flowcell transition zone of the visual analyzer so as to produce a sample fluid stream enveloped by the PIOAL. The PIOAL can include a fluid having a higher viscosity than the viscosity of the blood sample fluid. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, is effective to provide a target imaging state in at least some of the plurality of particles at an imaging site of the visual analyzer while a viscosity agent in the PIOAL retains viability of cells in the sample fluid stream leaving structure and content of the cells intact when the cells extend from the sample fluid stream into the flowing sheath fluid. In some cases, the viscosity agent of the sheath fluid includes glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes polyvinylpyrrolidone (PVP). In some cases, the polyvinylpyrrolidone (PVP) is at a concentration of 1% (w/v). In some cases, the viscosity agent of the sheath fluid further includes glycerol. In some cases, the viscosity agent of the sheath fluid includes glycerol at a concentration of 5% (v/v) and glycerol and polyvinylpyrrolidone (PVP) at a concentration of 1% (w/v). In some cases, the PIOAL has a viscosity of between about 1-10 centipoise (cP).

In yet another aspect, embodiments of the present invention encompass a particle and intracellular organelle alignment liquid (PIOAL) for use in a visual analyzer configured to direct flow of a sample of a given viscosity in a flow path. The PIOAL can include a fluid having a higher viscosity than the viscosity of the sample. The PIOAL can be effective to support the flow of the sample and to align particles and increase the in-focus content of particles and intracellular organelles of cells flowing in the flowpath, whereby the aligned particles and intracellular organelles of cells can be imaged. In some cases, the PIOAL further includes a viscosity agent. In some cases, the PIOAL further includes a buffer, a pH adjusting agent, an antimicrobial agent, an ionic strength modifier, a surfactant, and/or a chelating agent. In some cases, the particle and intracellular organelle alignment liquid is isotonic. In some cases, the particle and intracellular organelle alignment liquid includes sodium chloride. In some cases, wherein the sodium chloride is present at a concentration of about 0.9%. In some cases, the pH of the PIOAL sample is between about 6.0 to about 8.0 under operating conditions. In some cases, the pH of the PIOAL sample mixture is between about 6.5 to about 7.5 under operating conditions. In some cases, the PIOAL includes a pH adjusting agent for adjusting the pH is between about 6.8 to about 7.2 under operating conditions. In some cases, the PIOAL liquid has a target viscosity of between about 1-10 centipoise under operating conditions.

In still yet another aspect, embodiments of the present invention encompass a stock solution of concentrated PIOAL. In some cases, the concentrated stock solution can be diluted to achieve the target viscosity. In some cases, the concentration of the stock solution is present at least about 1.1× to at least about 100× concentration of the PIOAL under operating conditions. In some cases, the viscosity agent is selected from at least one of glycerol, glycerol derivative; PVP, CMC, ethylene glycol; propylene glycol (dihydroxypropane); polyethylene glycol; water soluble polymer and dextran. In some cases, the viscosity agent includes glycerol. In some cases, the viscosity agent includes glycerol and polyvinylpyrrolidone (PVP). In some cases, the viscosity agent includes glycerol and carboxymethylcellulose (CMC). In some cases, the viscosity agent includes glycerol and dextran sulfate. In some cases, the viscosity agent includes a glycerol derivative. In some cases, the viscosity agent includes PVP. In some cases, the viscosity agent includes propylene glycol (dihydroxypropane). In some cases, the viscosity agent includes polyethylene glycol. In some cases, the viscosity agent includes water soluble dextran. In some cases, the glycerol is present at a final concentration between about 1 to about 50% (v/v) under operating conditions. In some cases, said glycerol is present at a final concentration between about 3 to about 30% (v/v) under operating conditions. In some cases, said glycerol is present at a final concentration of about 30% (v/v) under operating conditions. In some cases, said glycerol is present at a final concentration of about 6.5% v/v under operating conditions. In some cases, said glycerol is present at a final concentration of about 5% v/v and the PVP is present at a concentration of about 1% w/v under operating conditions. In some cases, said PVP is present at a final concentration of about 1% w/v under operating conditions. In some cases, embodiments of the present invention encompass kits that include a PIOAL as disclosed herein.

In another aspect, embodiments of the present invention encompass methods for analyzing a plurality of cells in a blood fluid sample having a sample fluid viscosity, the cells having opposed major surfaces. Exemplary methods can include flowing a sheath fluid along a flowpath of a flowcell. The sheath fluid can have a sheath fluid viscosity higher than the sample fluid viscosity. Methods can also include injecting the blood fluid sample into the flowing sheath fluid within the flowcell. The plurality of cells can include a first subset with major surfaces oriented transverse to an orientation of an imaging path. Methods can also include imaging the particles along the imaging path at an imaging site while the plurality of cells include a second subset with the major surfaces transverse to the imaging path, the second subset being more numerous than the first subset. Methods can also include directing the fluid blood sample and the sheath fluid through a reduction in flowpath size such that an interaction between the sheath fluid and the sample fluid associated with the differing viscosities reorients at least some of the plurality of cells such that the second subset is more numerous than the first subset.

In another aspect, embodiments of the present invention encompass systems for imaging a plurality of cells in a blood fluid sample having a sample fluid viscosity. Systems can be configured for use with a sheath fluid having a sheath fluid viscosity higher than the sample fluid viscosity, the cells having opposed major surfaces. Exemplary systems can include a flowcell having a flowpath and a sample fluid injection tube, a sheath fluid input in fluid communication with the flowpath of the flowcell so as to transmit a flow of the sheath fluid along the flowpath of the flowcell, and a blood fluid sample input in fluid communication with the injection tube of the flowcell so as to inject a flow of the blood fluid sample into the flowing sheath fluid within the flowcell such that the plurality of the injected cells including a first subset with major surfaces aligned transverse to an orientation of an imaging path. In some cases, the flowpath of the flowcell can have a zone with a change in flowpath size configured such that an interaction between the sheath fluid and the blood sample fluid associated with the differing viscosities reorients at least some of the particles. Systems can also include an imaging device that images the plurality of particles along the imaging path at an imaging site while the major surfaces of the second subset of the plurality of cells are oriented transverse to the imaging path.

In one aspect, this invention relates to a method for imaging a particle comprising: treating particles in a sample using the particle contrast agent compositions of this disclosure; illuminating the stained particle with light in a visual analyzer comprising a flowcell and autofocus apparatus; obtaining a digitized image of the particle enveloped in a particle and/or intracellular organelle alignment liquid (PIOAL); and; analyzing a particle in the sample based on the image information. In some embodiments, the particle is selected from at least one of neutrophil, lymphocyte, monocyte, eosinophil, basophil, platelet, reticulocyte, nucleated red blood cell (RBC), blast, promyelocyte, myelocyte, metamyelocyte, red blood cell (RBC), platelet, cell, bacteria, particulate matter, cell clump, or cellular fragment or component. For example, in some embodiments, the apparatus may be used for automated image based white blood cell (WBC) differential counting, as well as automated identification of morphological abnormalities useful in determining, diagnosing, prognosing, predicting, and/or supporting a diagnosis of whether a subject is healthy or has a disease, condition, or infection and/or is responsive or non-responsive to treatment.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 4A, 4B-1, and 4B-2 depict aspects of flowcells according to embodiments of the present invention.

FIGS. 4A-1 and 4A-2 depict cross-section views of sheath fluid (e.g. PIOAL) envelope and sample fluidstream dimensions within a flowcell at a cannula exit port and an image capture site, respectively, according to embodiments of the present invention.

FIGS. 4C-4G, and 4D-1 depict aspects of cannula configurations according to embodiments of the present invention.

FIGS. 4H, 4I, and 4J depict aspects of results obtained using sheath fluid compositions, methods, and/or systems according to embodiments of the present invention.

FIGS. 4K-1, 4K-2, and 4K-3 depict aspects of sheath fluid and sample flow within a flowcell at an image capture site according to embodiments of the present invention.

FIG. 4L-1 depicts aspects of fluid flow velocity within a flowcell according to embodiments of the present invention.

FIGS. 4P and 4Q show comparison of images obtained using PIOAL versus images obtained using standard sheath fluid. It can be seen that use of PIOAL resulted in an improved RBC alignment.

FIGS. 5A and 5B illustrate aspects of sheath fluid and sample fluid flow characteristics, according to embodiments of the present invention.

DETAILED DESCRIPTION OF THE INVENTION

The present disclosure relates to apparatus, systems, compositions, and methods for analyzing a sample containing particles. In one embodiment, the invention relates to an automated particle imaging system which comprises an analyzer which may be, for example, a visual analyzer. In some embodiments, the visual analyzer may further comprise a processor to facilitate automated analysis of the images.

According to this disclosure, a system comprising a visual analyzer is provided for obtaining images of a sample comprising particles suspended in a liquid. The system may be useful, for example, in characterizing particles in biological fluids, such as detecting and quantifying erythrocytes, reticulocytes, nucleated red blood cells, platelets, and white blood cells, including white blood cell differential counting, categorization and subcategorization and analysis. Other similar uses such as characterizing blood cells from other fluids are also encompassed by embodiments of the present invention. Typically, the blood fluid sample is introduced into a flowing sheath fluid, and the combined sheath and sample fluids are compressed with a narrowing flowpath transition zone that reduces the thickness of the sample ribbon fluid flow. Hence, particles such as cells can be oriented and/or compressed within the blood fluid sample by the surrounding viscous sheath fluid, for example in combination with a geometric focusing effect provided by a narrowing transition zone. Similarly, internal features within blood cells can be aligned an oriented as a result of a viscosity differential between the sample fluid and the sheath fluid, for example in combination with a geometric focusing effect provided by a narrowing transition zone.

To facilitate the capacity, speed and effectiveness by which particles such as cells are categorized and/or subcategorized, it is advantageous to provide clear high quality images of the blood cells for automated analysis by the data processing system. According to the present disclosure, a prepared sample stream is arranged in a thin ribbon having a stable position between opposite walls of a flowcell. The positioning of the sample stream and its flattening into a thin ribbon shape may be achieved by flow between layers of a PIOAL introduced into the flowcell that differs in viscosity from the sample fluid and is flowed through a symmetrical narrowing transition zone of a flow channel.

Hematology—Particle Analysis System

Figure 1:
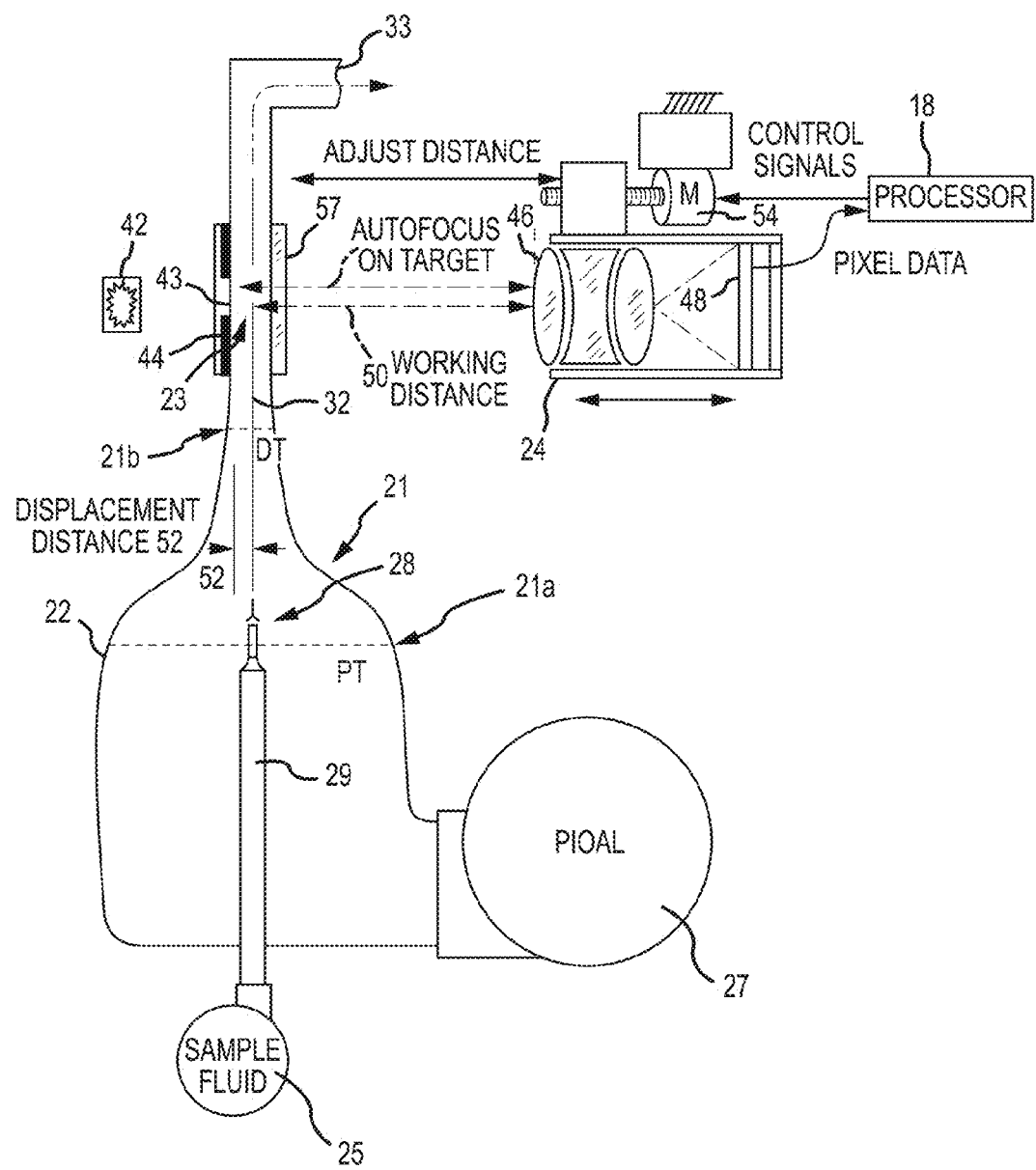
FIG. 1 is a schematic illustration, partly in section and not to scale, showing operational aspects of an exemplary flowcell, autofocus system and high optical resolution imaging device for sample image analysis using digital image processing.

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAL to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

According to some embodiments, the system can operate to hydrofocus the sample fluid ribbon 32. The term hydrofocus or hydrofocusing can refer to a focusing effect which is influenced by a viscosity difference between the sheath and sample fluids, a geometric narrowing transition zone of the flowcell, and a velocity difference between the sheath and sample fluids. Hydrodynamic flow results from the velocity difference between the sample and sheath fluid streams, which affects the flow ribbon thickness and shape.

Flowcell

Figure 2:
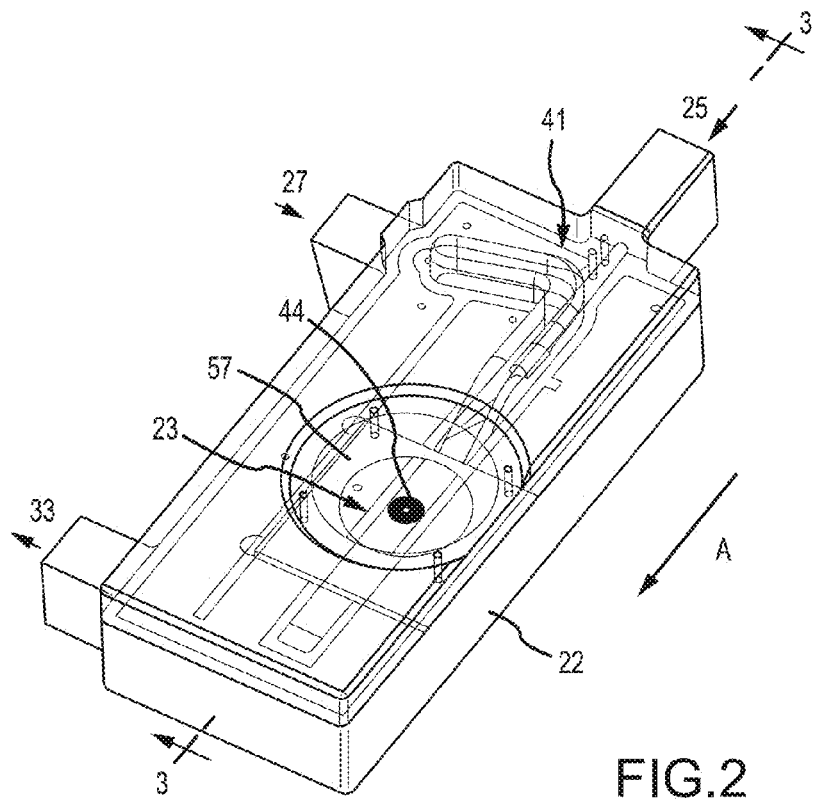
FIG. 2 is a perspective illustration of a flowcell according to an exemplary embodiment.
Figure 3:
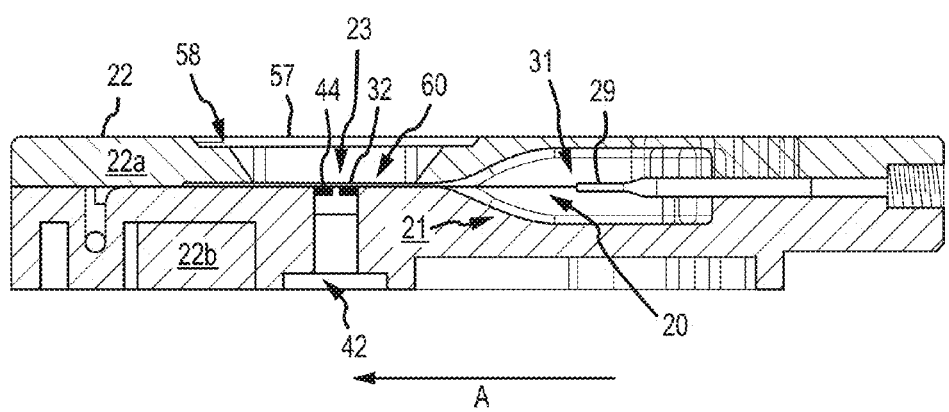
FIG. 3 is a longitudinal median section view along lines 3-3 of the flowcell shown in FIG. 2.

A practical embodiment of flowcell 22 is further depicted in FIGS. 2 and 3. As shown here, flowcell 22 can be coupled with a sample source 25 and also to a source 27 of PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an autofocus pattern 44. Flowcell 22 also has a rounded or recessed seat 58 which is configured to accept or receive a microscope objective (not shown).

According to some embodiments, the autofocus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed from a single piece of material. Alternatively, flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 μm to about 170 μm. As noted above, the pane 60 can define or form part of the flowpath or sheath (e.g. PIOAL) channel. By using a thin pane 60, it is possible to place the microscope objective very close to the sample fluid ribbon, and hence obtain highly magnified images of particles flowing along the flowpath.

Figure 3A:
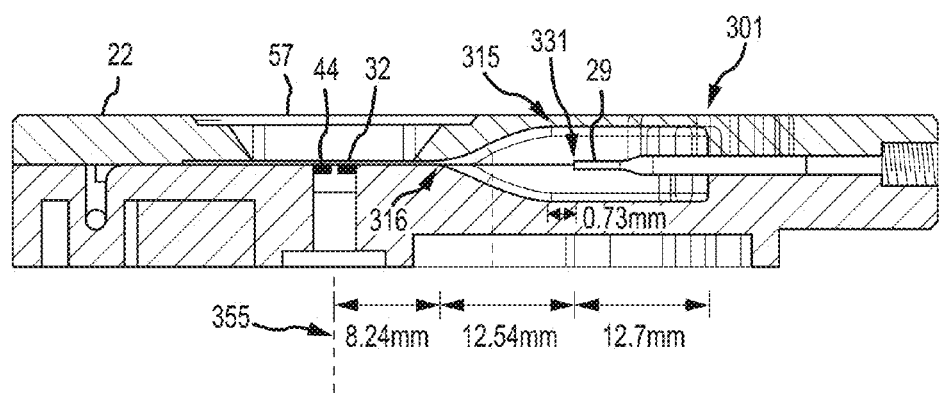
FIGS. 3A and 3B provide additional section views of flowcells according to embodiments of the present invention.
Figure 3B:
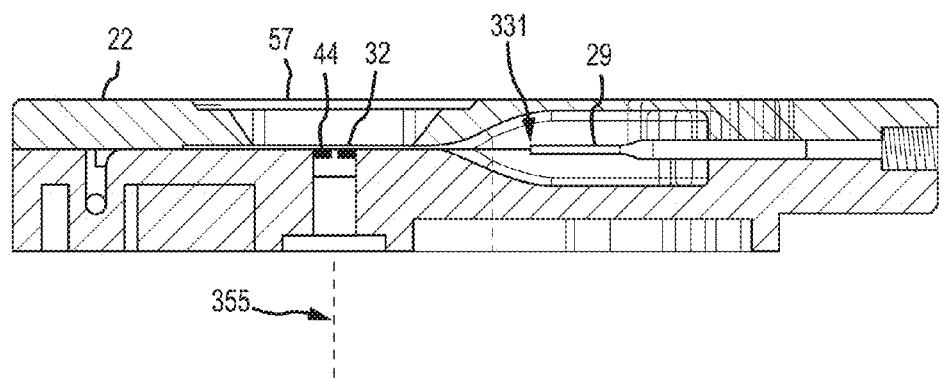

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream. White blood cells may have a diameter around 10 μm, for example. By providing a ribbon-shaped sample stream with a thickness less than 10 μm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 μm, and/or the internal flowpath produces a ribbon-shaped sample stream width of 500-3,000 μm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 μm in thickness, and/or the internal flowpath results in the ribbon-shaped sample stream of 2000 μm in width. These dimensions are particularly useful for hematology. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
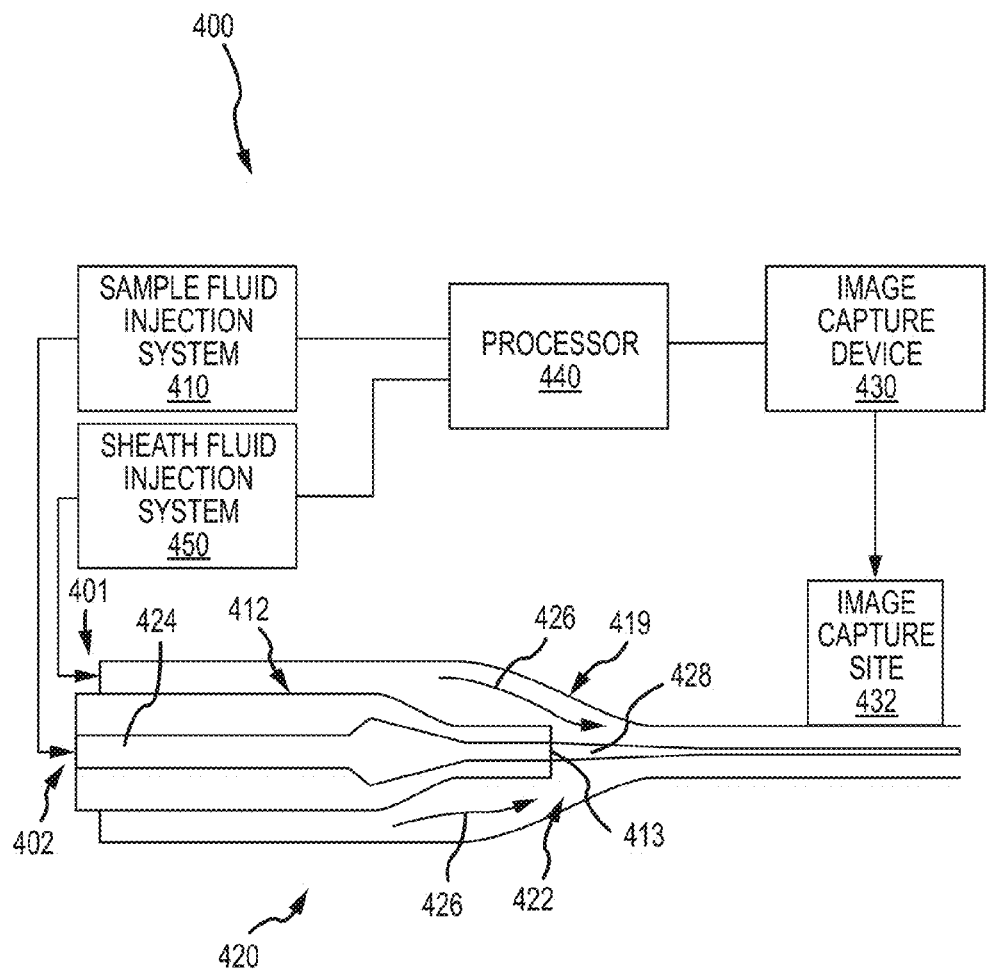
FIG. 4 depicts aspects of an analyzer system according to embodiments of the present invention.

FIG. 4 depicts aspects of a system 400 for imaging particles in a blood fluid sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422 (e.g. via sample fluid entrance 402), and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450 (e.g. via sheath fluid entrance 401). For example, the processor 440 may include or be in operative association with a storage medium having a computer application that, when executed by the processor, is configured to cause the sheath fluid injection system 450 to inject sheath fluid 426 into the flowcell 420. As depicted in FIG. 4, the distal exit port 413 of cannula 412 can be positioned at a central location along the length of the narrowing transition zone 419. In some cases, the distal exit port can be positioned more closely to the beginning (proximal portion) of the transition zone 419. In some cases, the distal exit port can be positioned more closely to the end (distal portion) of the transition zone 419. In some cases, the distal exit port 413 can be positioned entirely outside of the transition zone 419, for example as depicted in FIG. 3A (where distal exit port 331 is disposed proximal to the narrowing transition zone).

The sample fluid stream 428 has a first thickness T1 adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality the particles.

Accordingly, embodiments of the present invention encompass a system 400 for imaging a plurality of particles in a blood fluid sample 424 having a sample fluid viscosity The system 400 can be used with a sheath fluid 426 having a sheath fluid viscosity that differs from the sample fluid viscosity by a viscosity difference in a predetermined viscosity difference range. The system 400 can include a flowcell 420 having a flowpath 422 and a sample fluid injection tube 412. The flowpath 422 can have a reduction in flowpath size or narrowing transition zone. Further, the system 400 can include a sheath fluid input 401 in fluid communication with the flowpath 422 of the flowcell 420 so as to transmit a flow of the sheath fluid along the flowpath 422 of the flowcell 420. The system 400 can also include a blood fluid sample input 402 in fluid communication with the injection tube 412 of the flowcell 420 so as to inject a flow or stream 428 of the blood fluid sample into the flowing sheath fluid 428 within the flowcell 420. For example, the sample fluid 424 can exit the distal exit port 423 of the cannula 412 and into an envelope of the flowing sheath fluid 426 to form a sample ribbon 428 therein.

As the sheath fluid 426, along with the sample fluid ribbon 428 formed from the sample fluid 424, flow through a reduction 419 in flowpath size and toward an imaging site 432, a viscosity hydrofocusing effect induced by an interaction between the sheath fluid 426 and the sample fluid 424 associated with the viscosity difference, in combination with a geometric hydrofocusing effect induced by an interaction between the sheath fluid 426 and the sample fluid 424 associated with the reduction in flowpath size, provides a target imaging state in at least some of the plurality of particles at the imaging site 432. As shown here, the system 400 also includes an imaging device 430 that images the plurality of particles at the imaging site 432.

Figure 4A:
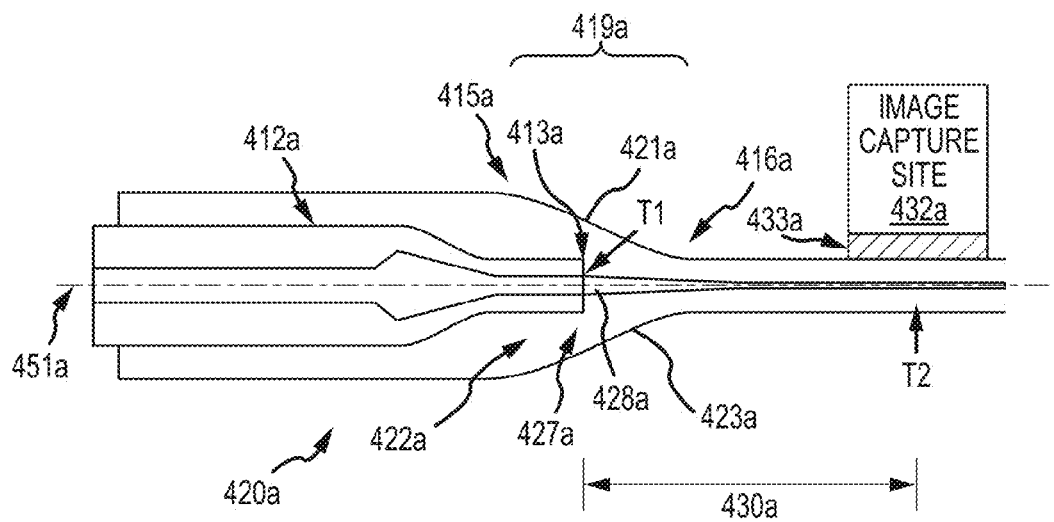

As shown in the flowcell embodiment depicted in FIG. 4A, a decrease in flowpath size (e.g. at transition zone 419a) can be defined by opposed walls 421a, 423a of the flowpath 422a. The opposed walls 421a, 423a can angle radially inward along the flowpath 422a, generally symmetric about a transverse plane 451a that bisects the sample fluid stream 428a. The plane 451a can bisect the sample stream 428a where the sample stream has a first thickness T1, at a location where the sample stream 428a exits a distal portion 427a of the cannula or sample injection tube 412a. Similarly, the plane 451a can bisect the sample stream 428a where the sample stream has a second thickness T2, at a location where the sample stream 428a passes the image capture site 432a. According to some embodiments, the first thickness T1 has a value of about 150 µm and the second thickness T2 has a value of about 2 µm. In such cases, the compression ratio of the sample ribbon stream is 75:1. According to some embodiments, the first thickness T1 has a value within a range from about 50 µm to about 250 µm and the second thickness T2 has a value within a range from about 2 µm to about 10 µm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon. As depicted in FIG. 4A, the distal exit port 413a of cannula 412a can be positioned at a central location along the length of the narrowing transition zone 419a. In some cases, the distal exit port can be positioned more closely to the beginning (proximal portion 415a) of the transition zone 419a. In some cases, the distal exit port can be positioned more closely to the end (distal portion 416a) of the transition zone 419a. In some cases, the distal exit port 413a can be positioned entirely outside of the transition zone 419a, for example as depicted in FIG. 3A (where distal exit port 331 is disposed proximal to the narrowing transition zone).

As depicted in FIG. 4A (as well as in FIGS. 4 and 4B-1), the transition zone 419a can be defined by an angular transitions at the proximal (415a) and distal (416a) portions. It is also understood that the transition zone 419a can instead present smooth or curved transitions at the proximal (415a) and distal (416a) portions, similar to the smooth or curved transitions as depicted in FIGS. 1, 3, 3A, 3B, and 4B-2).

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430a between the distal cannula portion 427a and the image capture site 432a. According to some embodiments, the distal portion 427a of the sample fluid injection tube 412a can be positioned at an axial separation distance 430a from the image capture site 432a, where the axial separation distance 432a has a value of about 21 mm. In some cases, the axial separation distance 430a has a value within a range from about 16 mm to about 26 mm.

The axial separation distance 430a between the cannula exit port and image capture site can impact the transition time for the sample fluid as the fluid travels from the exit port to the image capture site. For instance, a relatively shorter axial separation distance 430a can contribute to a shorter transition time, and a relatively longer axial separation distance 430a can contribute to a longer transition time.

The position of the exit port at the cannula distal portion 427a relative to the flowpath transition zone 419a, or relative to the proximal portion 415a of the flowpath transition zone 419a, can also inference the transition time for the sample fluid as the fluid travels from the exit port to the image capture site. For example, the sheath fluid may have a relatively slower speed at the proximal portion 415a, and a relatively faster speed at a location between the proximal portion 415a and the distal portion 416a. Hence, if the cannula exit port at distal portion 427a is positioned at the proximal portion 415a, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415a) of the flowcell, the longer it takes the sample to reach the image capture site. Conversely, if the cannula exit port at distal portion 427a is positioned distal to the proximal portion 415a (e.g. at a central location between proximal portion 415a and distal portion 416a, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419a, due to the narrowing cross-sectional area of the zone 419a.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amount of time (e.g. images per minute).

Although there are advantages associated with positioning the exit port of the cannula distal portion 427a more closely to the image capture site 432a, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficiently stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427a of the sample fluid injection tube 412a can be positioned distal to a proximal portion 415a of the flowpath transition zone 419a. Relatedly, the downstream end 427a of the sample fluid injection tube 412a can be positioned proximal to a distal portion 416a of the flowpath transition zone 419a. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the blood fluid sample. For example, such symmetry can be effective to limit red blood cells imaging orientation misalignment in the blood fluid sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 150 μm×150 μm and 400 μm×400 μm. In some cases, the image capture site 432a has a field of view 433a of about 275 μm×275 μm. In some cases, the field of view can be defined in terms of length times width. If expressed as surface area, a 275 μm×275 μm field of view has an area of 75,625 μm². According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

FIGS. 4A-1 and 4A-2 illustrate the effects of hydrofocusing on the sample stream as it travels from the cannula exit port to the image capture site. As shown in FIG. 4A-1, the sample stream can have a height H(S) of about 150 μm and a width W(S) of about 1350 μm. Further, the PIOAL sheath stream can have a height H(P) of about 6000 μm and a width W(P) of about 4000 μm. Subsequent to the hydrofocusing, as shown in FIG. 4A-2, the sample stream can have a height H(S) of about 2 μm and a width W(S) of about 1350 μm. Further, the PIOAL sheath stream can have a height H(P) of about 150 μm and a width W(P) of about 4000 μm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 μm and a width W(P) of about 4000 μm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 μL/second. The volumetric flow rate of sample fluid at the imaging area can be about 0.232 μL/second. In some cases, the cross-sectional area of the combined sheath and sample streams at the imaging site is 600,000 μm². In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 μL/s and the fluid sample can flow at a fluid sample volumetric flow rate of 0.232 μL/s (or within a range from 0.2 to 0.35 μL/s). In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath fluid and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

Figures 1, 2, 4B:
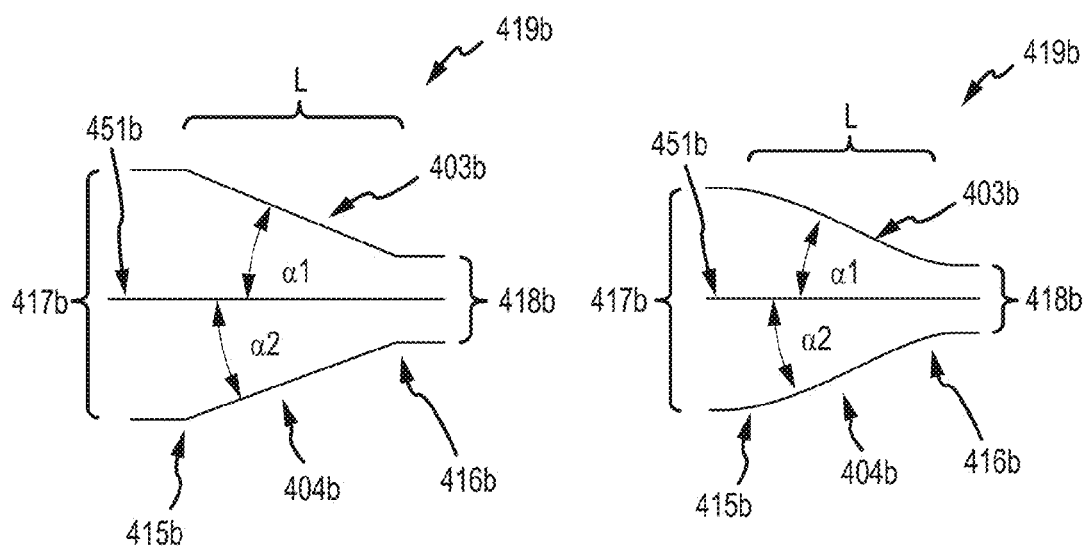
Figures 1, 4A:
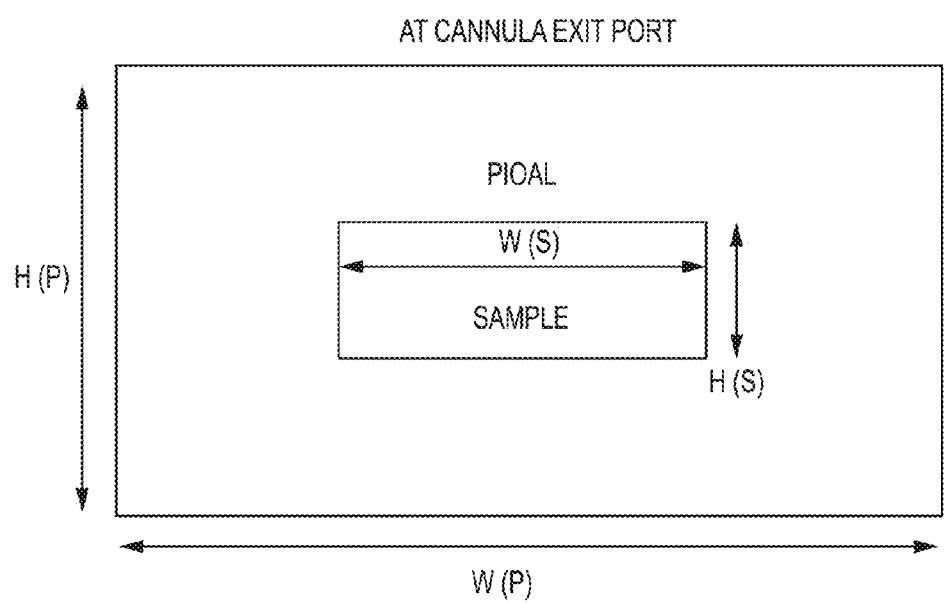
Figures 2, 4A:
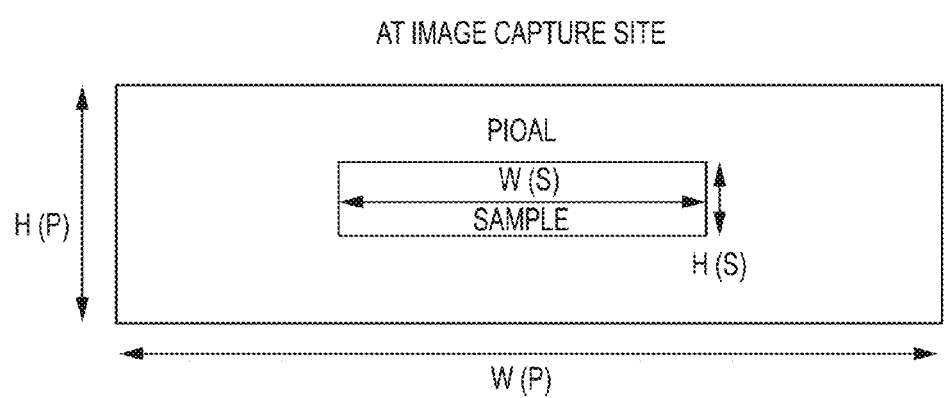

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial views of FIGS. 4B-1 and 4B-2, the transition zone 419b of the flowpath can have a length L between a proximal portion 415b and a distal portion 416b, where the proximal portion 415b has a proximal height 417b, and the distal portion 416b has a distal height 418b. As depicted in FIG. 4B-2, and as noted elsewhere herein, the shape or contour of the transition zone can be curved or smooth, and for example can be provided in the shape of an S-curve, a sigmoidal curve, or a tangent curve. According to some embodiments, the proximal height 417b has a value of about 6000 μm. In some cases, the proximal height 417b has a value within a range from about 3000 μm to about 8000 μm. According to some embodiments, the distal height 418b has a value of about 150 μm. In some cases, the distal height 418b has a value within a range from about 50 μm to about 400 μm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figure 4C:
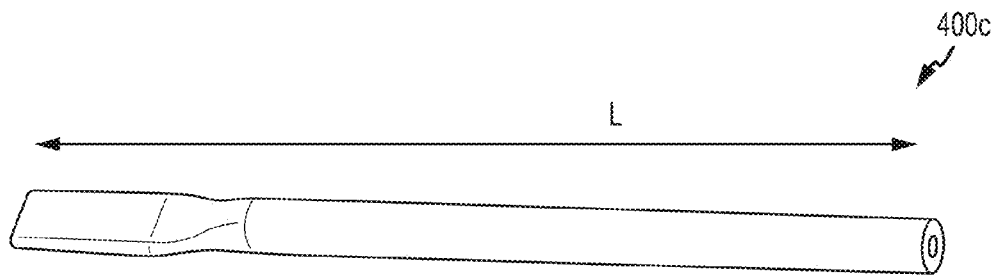
Figure 4D:
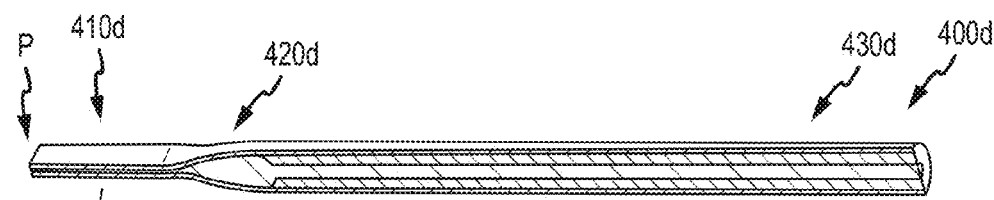

FIG. 4C depicts features of an exemplary cannula or sample feed tube 400c according to embodiments of the present invention, where the cannula has a length L. FIG. 4D depicts a longitudinal cross-section of cannula 400d. As shown here, the cannula 400d includes a distal flattened section 410d, a central tapered section 420d, and a proximal tubular portion 430d. As depicted in FIG. 4C-1, an exemplary cannula or sample feed tube 400c-1 can have a distal portion 410c-1 and a proximal portion 430c-1. In some cases, the distal portion 410c-1 has a length of about 1.359 mm and a width of about 1.43 mm. In some cases, the exit port of the distal end has an exit width W(E) of about 1.359 mm. According to some embodiments, a cannula may have an internal flowpath geometry that is different from what is depicted in FIGS. 4C and 4D. For example, as illustrated in FIG. 4D-1, the cannula 400d-1 does not include a tapered central section having an expanded flow area cross-section. As depicted in FIG. 4D-1, cannula 400d-1 has a distal section 410d-1, a central tapered section 420d-1 having a tapering inner diameter, and a proximal section 430d-1. Corresponding to the tapering inner diameter of central section 420d-1, the cross-sectional inner area of 410d-1 is smaller than the cross-sectional inner area of 430d-1.

A hematology system according to embodiments of the present invention can process a blood sample having a volume of about 150 μL. The aspirated blood volume can be about 120-150 μL. In some cases, the minimum available blood volume in the sample tube is about 500 μL for an automatic sampling mode and about 250 μL for manual sampling mode. The cannula or injection tube 400d shown in FIG. 4D has an internal volume of about 13 uL. According to some embodiments, the cannula or injection tube has an internal volume of less than about 30 uL.

Figure 4E:
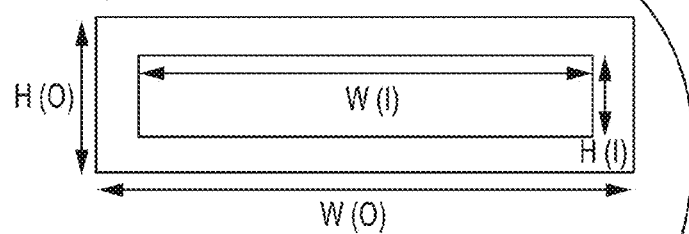

FIG. 4E illustrates a transverse cross-section of a distal flattened section 410e. As shown here, the distal section 410e has an inner width W(I) and an inner height H(I), through which a sample stream flows. Further, the distal section 410e has an outer width W(O) and an outer height H(O). As depicted in FIGS. 4D and 4E taken in combination, the distal portion 410e of the sample fluid injection tube has an outlet port P having a height H(I) and a width W(I), where the height H(I) is less than the width W(I). According to some embodiments, the height H(I) of the outlet port P of distal portion 410e (or the inner height of the distal portion 410d) can have a value of about 150 μm. In some cases, the height H(I) can be within a range from about 50 μm to about 250 μm. According to some embodiments, the width W(I) of the outlet port P of distal portion 410e (or the inner width of the distal portion 410d) can have a value of about 1350 μm. In some cases, the width is about 1194 μm. In some cases, the width W(I) can have a value within a range from about 500 μm to about 3000 μm. In some cases, distal flattened section 410d can be manufactured by applying a clamping force to a tube or conduit.

Figure 4F:
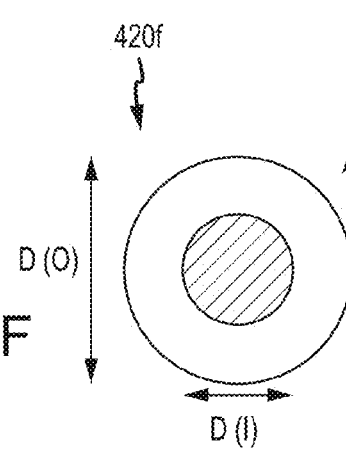
Figure 4G:
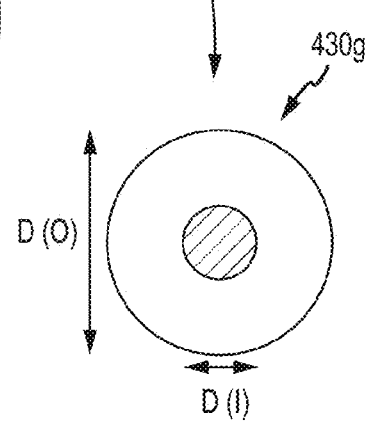
Figures 1, 4D:
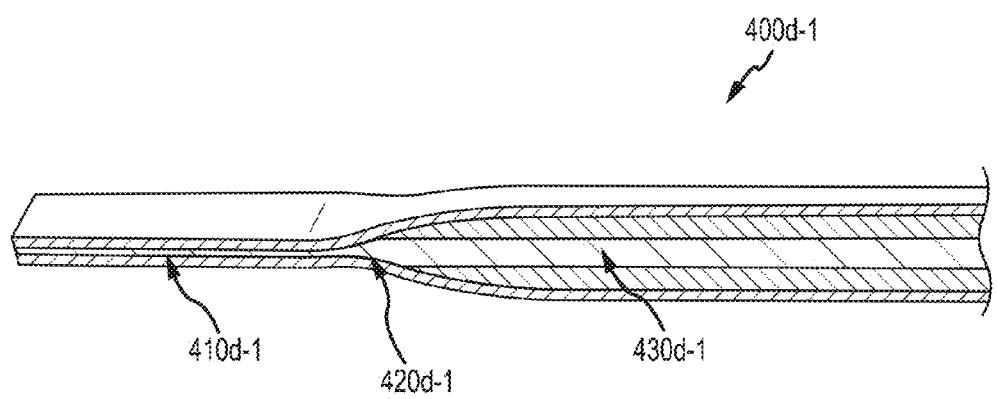

FIG. 4F illustrates a transverse cross-section of a central tapered section 420f. As shown here, the central tapered section 420f has an inner diameter D(I) through which a sample stream flows. Further, the central tapered section 420f has an outer diameter D(O). FIG. 4G illustrates a transverse cross-section of a proximal section 430g. As shown here, the proximal section 430g has an inner diameter D(I) through which a sample stream flows. Further, the distal section 430g has an outer diameter D(O).

As depicted in FIG. 4D, the injection tube or cannula 400*d* can have a proximal portion 430*d* having a first flow cross-section area (e.g. $\pi*(D/2)^2$ shown in FIG. 4G), a distal portion 410*d* having a second flow cross-section area (e.g. W(I)*H(I) shown in FIG. 4E) that is less than the first flow cross-section area, and a third portion 420*d* disposed between the proximal portion 430*d* and the distal portion 410*d*. The third portion 420*d* can have a third flow cross-section (e.g. $\pi*(D/2)^2$ shown in FIG. 4F) that is larger than the first and second flow cross-sections. In some instance, the outer diameter D(O) of proximal portion 430*g* is about 1067 μm and the inner diameter D(I) of proximal portion 430*g* is about 813 μm.

Cellular Structure, Content, and Alignment

According to some embodiments, to accomplish staining and visualization of white blood cells, it is helpful to lyse red blood cells in the sample and permeabilize the white blood cells so as to allow the stain to incorporate with the white blood cells. It is often desirable to obtain a stain of the white blood cells with little to no change in morphology to the cells. Further, it is often desirable to obtain staining properties which resemble a Wright stain. What is more, it is often desirable to obtain a high red cell alignment (e.g. target >90%).

FIG. 4H (upper panel) depicts results obtained using a stain formulation that does not include glutaraldehyde. It was observed that the cells fell apart as a result of shear forces encountered in the flowcell. Although a good stain of the nucleus was achieved, the nucleus itself appeared deformed, and the cell membrane appeared damaged. In sum, when imaged the cell appeared to be destroyed due to disruption to the cellular content and structure.

FIG. 4H (lower panel) depicts WBC results obtained using a stain formulation that includes glutaraldehyde. As shown here, the cell membranes are intact and the cells are round. Hence, it was observed that the version of the stain which did not use glutaraldehyde (e.g. shown in FIG. 4H, upper panel) resulted in resulting in weakened WBC's. Although the WBC's are more intact in FIG. 4H (lower panel) the nucleus portions are damaged.

The sheath fluid (PIOAL) used to obtain the FIG. 4H (lower panel) images included 30% glycerol. In contrast, the sheath fluid (PIOAL) used to obtain the FIG. 4I (upper panel) images included 6.5% glycerol. The lower concentration of glycerol resulted in a better morphology, with the nucleus mostly unchanged. Hence, it was observed that the cell membrane in FIG. 4I (upper panel) is even more intact that than the cell membrane in FIG. 4H (lower panel). The lower glycerol concentration in FIG. 4I (upper panel) can operate to reduce the viscosity difference, thereby reducing the shear force. If excessive shear force is present, the force can destroy the cell membranes. The glycerol may have some properties that are incompatible with the cells and thus a higher concentration of glycerol may also destroy the cell membranes. Hence, it is possible to conclude that the damage to the nucleus depicted in FIG. 4H (upper panel) can be the result of the 30% glycerol in the sheath fluid.

When the glycerol concentration was lowered to 6.5% as depicted in FIG. 4I (upper panel), however, the alignment of the red blood cells in the sample fluid was observed to diminish.

Various alternative PIOAL formulations were used in an attempt to obtain improved alignment in red blood cells, but these alternative formulations did not provide satisfactory results. For example, several different viscosity enhancers were tried, but many of them exhibited behavior similar to that of the higher 30% glycerol formulation, such that the cell contents were damaged.

It was discovered that by using polyvinylpyrrolidone (PVP) and 5% glycerol as a viscosity agent component, it was possible to obtain a sheath fluid having a viscosity that matched the viscosity of the 30% glycerol formulation (and hence improved alignment results were achieved) without the negative effects of destroying the nucleus. FIG. 4I (lower panel) depicts results obtained using a PIOAL with 5% glycerol and 1% PVP. Hence, it can be seen that the viscosity agent in the sheath fluid retains viability of cells in the sample fluid stream, leaving structure and content of the cells intact, for example when cells flow through the flowcell and are exposed to the flowing sheath fluid. According to some embodiments, the concentration percentage of glycerol is expressed in terms of (v/v) and the concentration percentage of PVP is expressed in terms of (w/v).

Figure 4J:
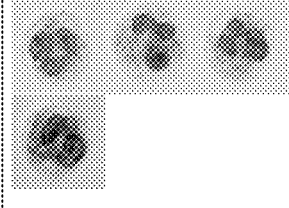

FIG. 4J depicts image capture results based on a traditional microscope wet mount technique (left column) as compared to a flowcell technique according to embodiments of the present invention (right column). The wet mount procedure can be considered as a target standard for image clarity and quality. It was observed that techniques involving sheath fluids and flow cell designed as disclosed herein were effective in achieving image clarity and quality equivalent to that of the wet mount procedure.

According to some embodiments, a flowstream ribbon can split when the viscosity differential between the sample fluid and the sheath fluid exceeds a certain threshold. According to some embodiments, a flowstream ribbon split was observed when using a sheath fluid containing glycerol at 60%.

Figure 4K:
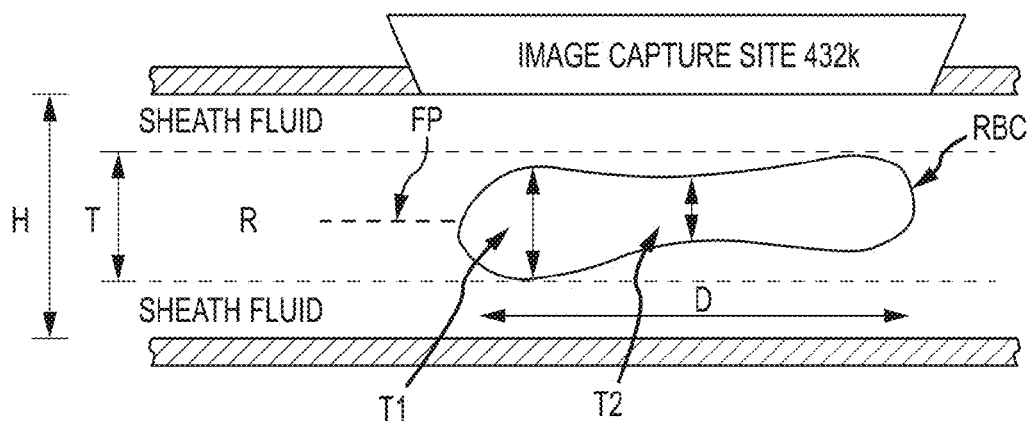
FIGS. 4K and 4L depict aspects of sheath fluid and sample flow within a flowcell at an image capture site, according to embodiments of the present invention.

As shown in FIG. 4K, a sample stream ribbon R flowing through an image capture site 432*k* of a flowcell 420*k* can have a thickness T of about 2 μm. In some cases, thickness T of the sample stream ribbon can be up to about 3 μm. Typically, cells or particles that are smaller than the sample stream thickness will be contained within the ribbon. An exemplary red blood cell (RBC) can be present as a biconcave disk and can have a diameter D of between about 6.2 μm and about 8.2 μm. Further, an exemplary red blood cell can have a maximum thickness T1 of between about 2 μm and about 2.5 μm and a minimum thickness T2 of between about 0.8 μm and about 1 μm. In some cases, red blood cells can have a thickness of up to about 3 μm. Exemplary human platelets can vary in size, and can also have a thickness or diameter of about 2 μm. Although not shown to scale here, the flowcell can define a flow path thickness H having a value of about 150 μm, at the image capture site. In some cases, the flowpath thickness F has a value between 50 μm and 400 μm. This flowpath thickness F can also correspond to the distal height 418*b* of distal portion 461*b* depicted in FIGS. 4B-1 and 4B-2.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 μm to 5 μm. A viscosity differential between the sheath fluid and the sample fluid can be selected so as to achieve a desired positioning of the ribbon sample stream within the flowcell.

Viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the blood fluid sample. For example, viscosity differentials can be effective to limit red blood cells imaging orientation misalignment in the blood fluid sample to less than about 10%. That is, 90 or more red blood cells out of 100 red blood cells in a sample can be aligned so that their major surfaces face toward the imaging device. A symmetrical narrowing transition zone can provide a value of 20%. As discussed elsewhere herein, for example with reference to FIG. 4R, it is possible to compare alignment results obtained from an analyzer configuration that involves a symmetrical narrowing flowcell transition zone and a viscous sheath fluid to alignment results obtained from an analyzer configuration that involves a symmetrical narrowing flowcell transition zone without the use of a viscous sheath fluid. Use of a viscous sheath fluid can reduce the percentage of misaligned cells. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14/216,533, the content of which is incorporated herein by reference.

Figure 4L:
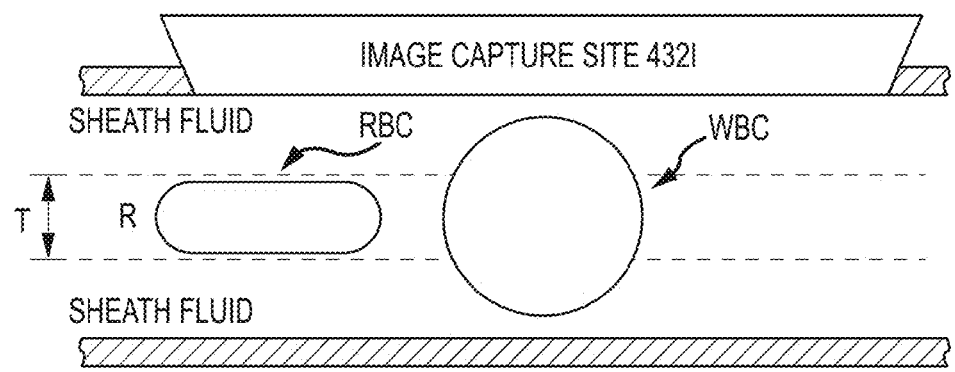
Figures 1, 4K:
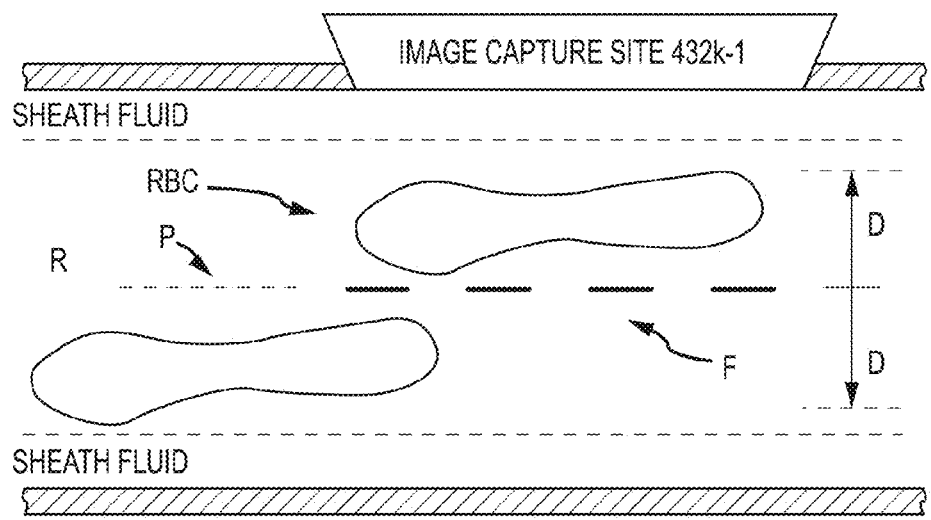
Figures 2, 4K:
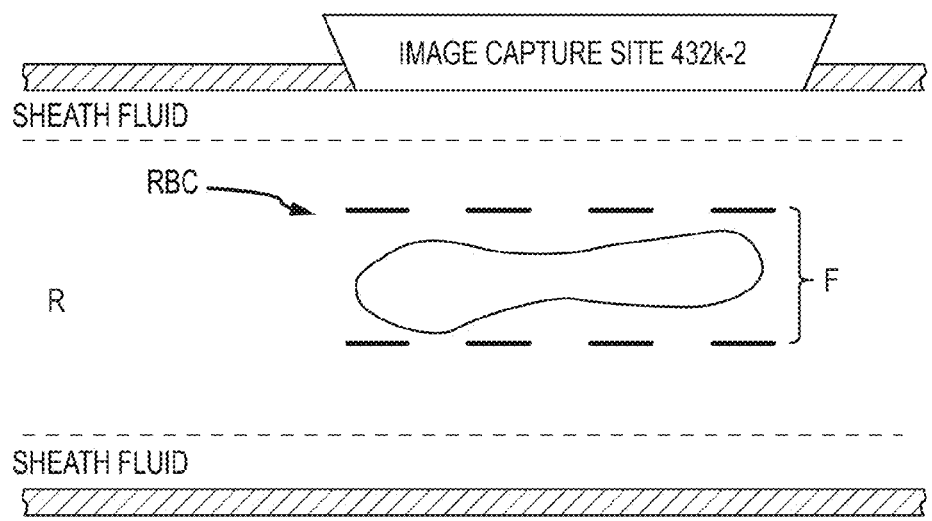
Figures 3, 4K:
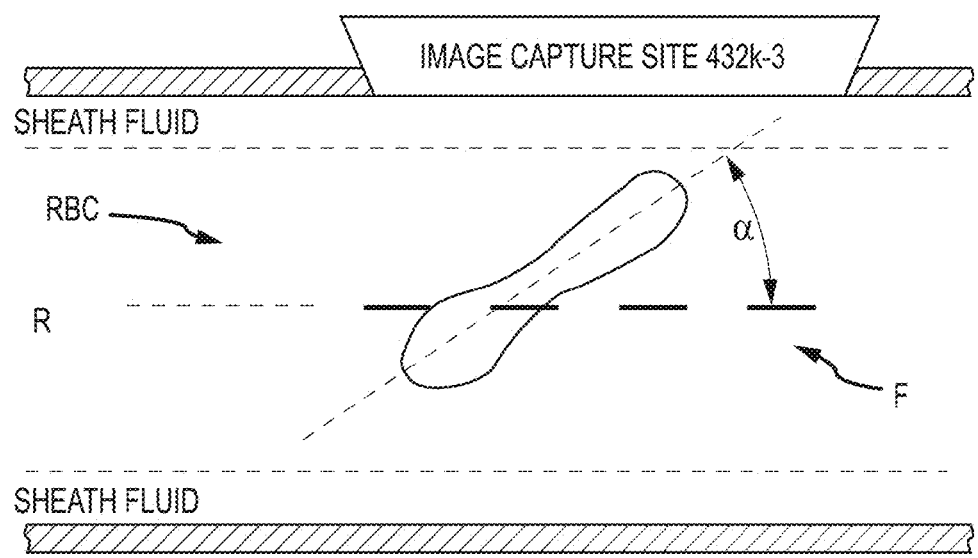
Figures 1, 4L:
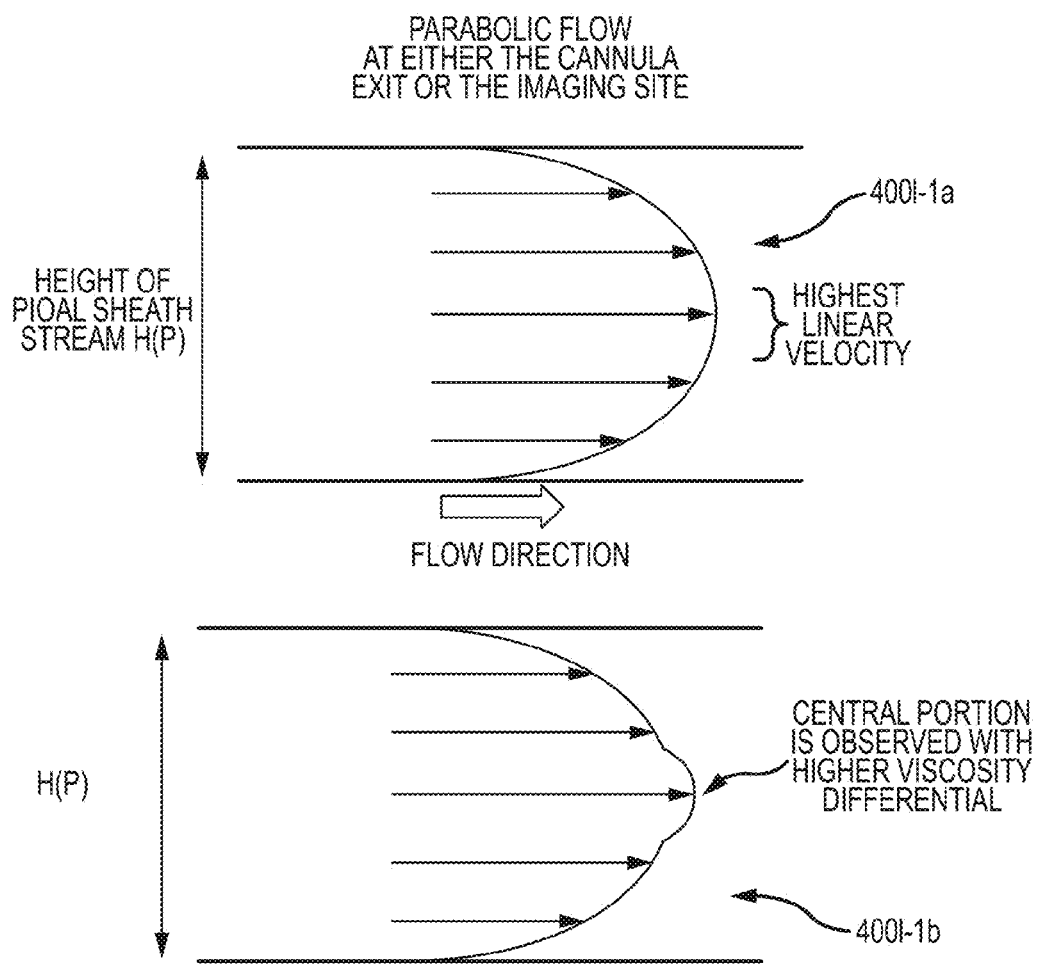

White blood cells are typically larger than red blood cells and platelets. For example, exemplary neutrophils and eosinophils can have a diameter of between about 10 μm and about 12 μm. Exemplary basophils can have a diameter of between about 12 μm and about 15 μm. Exemplary lymphocytes (small) can have a diameter of between about 7 μm and about 8 μm, and exemplary lymphocytes (large) can have a diameter of between about 12 μm and about 15 μm. Exemplary monocytes can have a diameter of between about 12 μm and about 20 μm. The configuration of the particle analysis system, including interaction between the sheath fluid and the fluid sample ribbon as they pass through the flowcell, can operate to compress white blood cells as they travel through the image capture site 432*l*, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid. The numerical values or ranges for the thickness T of sample stream ribbon R, and the thickness F of the flowpath as discussed above with regard to FIG. 4K are similarly applicable to FIG. 4L.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

As depicted in FIG. 4L, portions of a cell such as a white blood cell can extend into the sheath fluid. Embodiments of the present invention encompass sheath fluid compositions that do not lyse or shred the cell, or otherwise compromise the integrity of the outer cell membrane, when the cell is exposed to the sheath fluid. A viscosity agent in the sheath fluid can operate to retain viability of cells in the sample fluid stream, so as to leave the structure (e.g. shape) and the content (e.g. nucleus) of the cells intact when the cell membrane or wall traverses an interface between the sample fluid ribbon and the sheath fluid envelope or otherwise extends from the sample fluid stream into the flowing sheath fluid.

Often, there are compressive forces acting upon the cells or particles as they flow within the sample fluid ribbon along the flowcell. Hence, the cells may come into contact with the sheath fluid while the cells are in a compressed state or are otherwise subject to compressive forces as a result of a narrowing transition zone. The viscosity agent of the sheath fluid can operate to protect the compressed cells from being shredded or destroyed when they emerge from the thin sample fluid ribbon and become exposed to the viscous sheath fluid, at least until the cells reach the image capture site. Hence, the viscosity agent composition of the sheath fluid can operate as a cellular protectorant, while also enhancing alignment of the particles or intraparticle content.

With reference to FIGS. 4K and 4L, in some instances portions of the cell or particle may extend out of the thin sample fluid ribbon R and into the surrounding sheath fluid. As discussed elsewhere herein, the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. FIG. 4L-1 depicts exemplary aspects of parabolic flow profiles 400*l*-1*a* and 400*l*-1*b*. The parabolic profile 400*l*-1*a* in the upper panel is a typical velocity profile found in flows within certain flowcell embodiments of the present invention (e.g. where there is little or no viscosity differential between a sample fluid flowstream that is enveloped within a sheath fluid flowstream). As can be seen, a highest linear velocity is observed in the middle of the fluid stream and slower linear velocities are observed near the flowcell wall. Profile 400*l*-1*a* can also be observed in fluid stream with a slight viscosity difference between the sheath and sample fluids. In a case where there is a high viscosity differential between the sheath and fluid streams, a central bump is observed as shown in profile 400*l*-1*b*, where there is a localized central area with amplified linear velocities. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sample fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

As noted elsewhere herein, and with reference to FIGS. 4K and 4L, as the sheath fluid and the sample fluid R flow through a reduction in flowpath size or transition zone of a flowcell, and toward an imaging site 432*k* or 432*l*, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site 432*k* or 432*l*.

In some cases, the target imaging state is a target orientation relative to a focal plane F at the imaging site. For example, as depicted in FIG. 4K-1, the particle (RBC) can be displaced at a distance from the focal plane F. In some cases, the target orientation involves a target particle orientation relative to the focal plane F at the imaging site 432*k*-1. The particle can be a blood cell, such as a red blood cell, a white blood cell, or a platelet. As shown here, the flowpath at the imaging site 432*k*-1 can define a P plane that is substantially parallel to or coplanar with the focal plane F. In some cases, a portion of the particle may be positioned along the focal plane F, yet the central portion of the particle may otherwise be offset from the focal plane F. In some cases, the target orientation involves a target position relative to the focal plane F at the imaging site 432k-1. For example, the target position may involve positioning of the particle so that at least a portion of the particle is disposed along the focal plane F. In some cases, the target position may involve positioning of the particle so that a distance between the particle and the focal plane F does not exceed a certain threshold. In some cases, the target position involves a target particle position that is relative to the focal plane F at the imaging site 432k-1. In some cases, the target position is at or less than a distance D from the focal plane F, where distance D corresponds to a positional tolerance. A viscosity differential between the sheath fluid and the sample fluid can be selected so as to achieve a desired positioning of the ribbon sample stream within the flowcell (e.g. relative to flowpath plane P and/or focal plane F). In some cases, the viscosity differential can be selected so as to achieve a target particle position that is at or less than the positional tolerance D.

In some cases, the focal plane F has a thickness or depth of field as indicated in FIG. 4K-2, and the particle (RBC) has a target imaging state relative to the focal plane thickness. For example, the target position for the particle can be within the focal plane F or at least partially within the focal plane F. In some cases a high optical resolution imaging device or camera can have a depth of field or focal plane thickness of about 7 μm. In some cases, the depth of field or focal plane thickness has a value with a range from about 2 μm to about 10 μm. In some cases, the depth of the field of the camera is similar or equal to the sample ribbon thickness at the image capture site.

In some cases, the target orientation can involve a target alignment relative to the focal plane F at the imaging site. For example, the target alignment can indicate that a plane defined by the particle is aligned with the focal plane F, not to exceed a certain angle α relative to the focal plane F at the image capture site 432k-3 as shown in FIG. 4K-3. In some cases, the target imaging state can involve a limitation on the number or percentage of misaligned particles in a sample. For example, a difference in viscosity between the sheath fluid and the sample fluid R can be effective to limit red blood cells imaging orientation misalignment in the blood fluid sample to less than about 10%. That is, 90 or more red blood cells out of 100 red blood cells in a sample can be aligned so that their major surfaces face toward the imaging device (as depicted in FIGS. 4K-1 and 4K-2) or so that the alignment of those 90 or more RBCs is within 20 degrees from a plane substantially parallel to the direction of flow (e.g. RBC alignment angle α is 20 degrees or less). As discussed elsewhere herein, in some cases at least 92% of non-spherical particles such as RBCs can be aligned in a plane substantially parallel to the direction of flow. In some cases, at least between 75% and 95% of non-spherical particles such as RBCs can be substantially aligned, namely within 20 degrees from a plane substantially parallel to the direction of flow (e.g. alignment angle α is 20 degrees or less). According to some embodiments, 90% or more of certain particles (e.g. red blood cells and/or platelets) can be oriented transverse to the imaging axis of the imaging device.

In some cases, embodiments of the present invention include compositions for use with a hematology system as described herein, such as a sheath fluid or particle and intracellular organelle alignment liquid (PIOAL). Such sheath fluids or PIOALs are suitable for use in a combined viscosity and geometric hydrofocusing visual analyzer. The PIOAL can operate to direct or facilitate flow of a blood sample fluid of a given viscosity through a narrowing flowcell transition zone of the visual analyzer. The PIOAL can include a fluid having a higher viscosity than the viscosity of the sample. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, can be effective to provide a target imaging state in at least some of the plurality of particles at an imaging site of the visual analyzer while retaining viability of cells in the blood sample fluid.

Figure 4M:
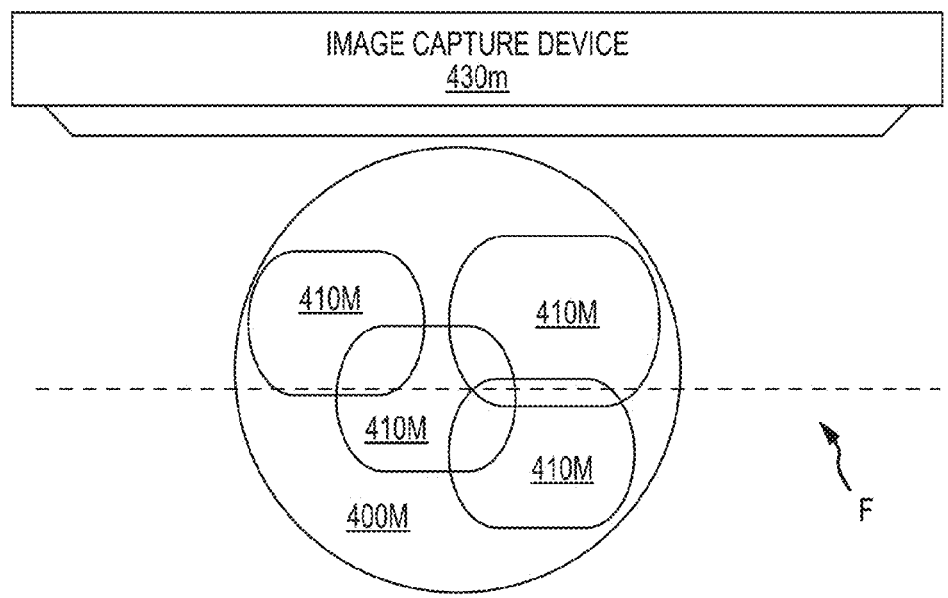
FIGS. 4M and 4N depict aspects of intracellular alignment and imaging, according to embodiments of the present invention.
Figure 4N:
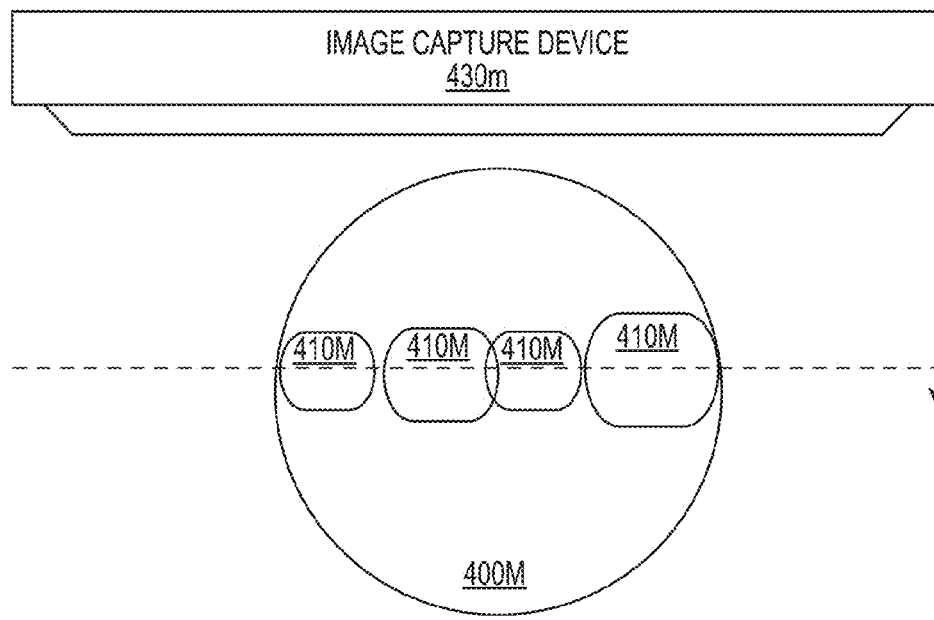

FIG. 4M depicts an exemplary neutrophil 400m (a type of white blood cell) having internal organelles such as lobes 410m. As a result of the viscosity differential between the sample fluid and the sheath fluid, the internal organelles can align within the cell, as indicated by FIG. 4N. Hence, the intracellular organelles can be effectively imaged with an image capture device 430m, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids. Accordingly, enhanced imaging results corresponding to cell alignment and in-focus are achieved using the viscosity differential, hydrodynamic flow, and geometric compression features.

As noted elsewhere herein, and with reference to FIGS. 4M and 4N, as the sheath fluid and the sample fluid R flow through a reduction in flowpath size or transition zone of a flowcell, and toward an imaging site of an image capture device 430m or 430n, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site. According to some embodiments, the target imaging state may correspond to a distribution of imaging states.

In some cases, the target imaging state can involve a target intraparticle structure orientation (e.g. alignment and/or position) relative to a focal plane at the imaging site. For example, as depicted in FIG. 4N, the internal structures 410m (e.g. intracellular structure, organelle, lobe, or the like) can be oriented relative to the focal plane F. In some cases, the target alignment involves a target intraparticle structure alignment relative to a focal plane F at the imaging site, similar to the particle alignment relationship depicted in FIG. 4K-3. In some cases, the target position involves a target intraparticle structure position relative to a focal plane at the imaging site, similar to the particle position relationship depicted in FIG. 4K-1. In some cases, the target orientation of the intraparticle structure can include both a target alignment relative to the focal plane and also a target position relative to the focal plane. In some cases, the target imaging state can involve a target deformation at the imaging site. For example, as depicted in FIG. 4N, the particle 400m has a compressed shape as compared to the particle shape depicted in FIG. 4M. Hence, it can be seen that operation of the flowcell can produce a lateral compression effect on the particle shapes. Relatedly, the intraparticle features can be positionally or directionally oriented (e.g. aligned with respect to the focal plane F and/or ribbon flow plane) as the particle itself is compressed in shape. According to some embodiments, a velocity difference between the sheath and sample fluids can produce friction within the flowstream, and a viscosity difference between the sheath and sample fluids can amplify that hydrodynamic friction.

EXAMPLES

Any of a variety of hematology or blood particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flowcell can support a 5-part WBC differential test. In some cases, images obtained using the flowcell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. For example, diagnostic or testing techniques can be used to differentiate various cells (e.g. neutrophils, lymphocytes, monocytes, eosinophils, basophils, metamyelocytes, myelocytes, promyelocytes, and blasts).

The Examples provided herein are for the purpose of illustration only, and the invention is not limited to these Examples, but rather encompasses all variations that are evident as a result of the teaching provided herein.

Prior to the experiments described herein, there was no published protocol that allows for the development and the methods of use comprising PIOAL for aligning particles and repositioning intracellular content as disclosed herein. This is useful for image-based analysis and differential categorization and subcategorization of particles in body fluid (e.g. blood) samples. The methods and compositions disclosed herein can optionally stain and/or lyse particles in a suitable manner to achieve white cell staining, reticulocyte staining and platelet staining, that mimic's Wright stained cells seen on a whole blood smear.

The exemplary compositions described herein allow staining to occurs at a relatively low blood to reagent dilution and the staining can occurs rapidly (e.g. within 30 sec). If desired, the exemplary method can employ the use of a surfactant in combination with heat to achieve red cell lysis. The exemplary formulations can be modified to retain RBC integrity and still achieve WBC, retic and platelet staining efficacy.

Aspects and embodiments of the present disclosure are based on the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties.

Figure 4O:
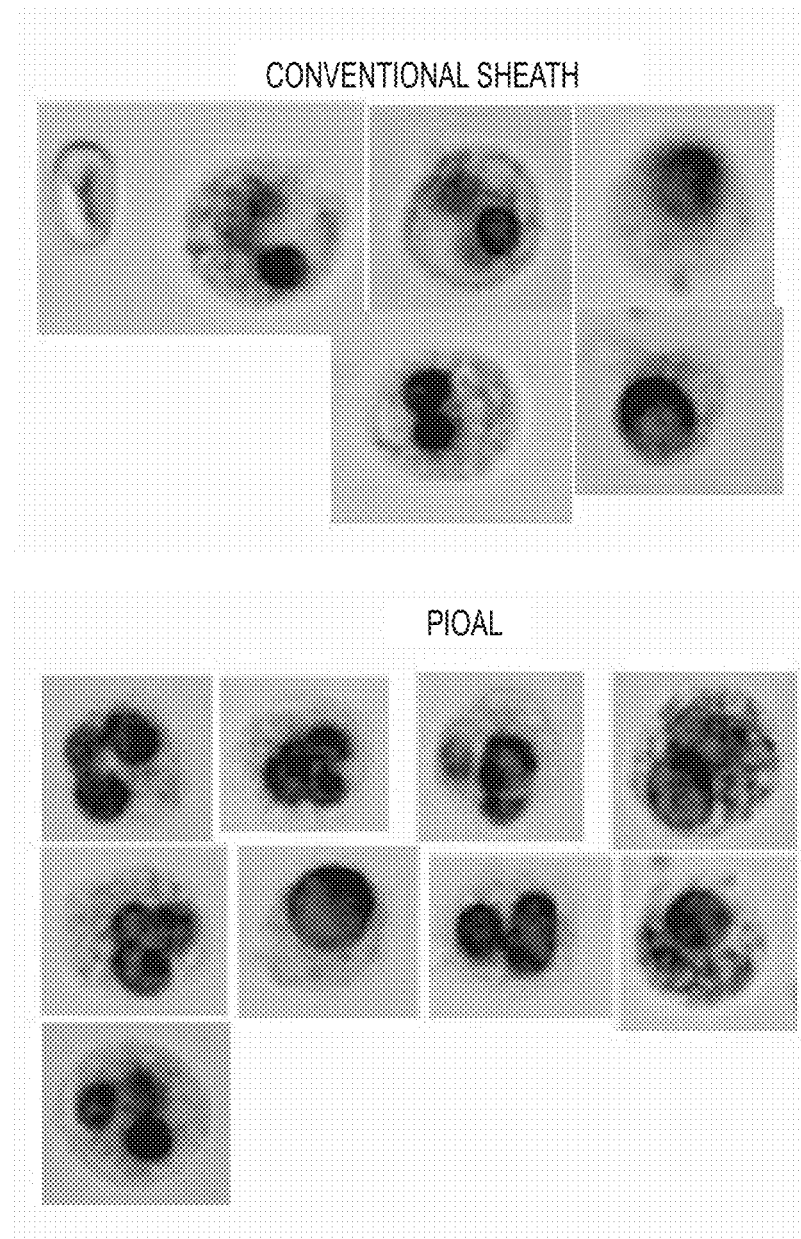
FIG. 4O depicts aspects of the effect of PIOAL on particle and/or intracellular particle alignment and imaging according to embodiments of the present invention. In this comparison of images obtained using PIOAL versus images obtained using a non PIOAL sheath fluid, it can be seen that use of the PIOAL resulted in more in-focus cellular contents such as lobes, cytoplasm, and/or granule.

FIG. 4O shows a comparison of images obtained using PIOAL versus images obtained using a non PIOAL sheath fluid. Use of the PIOAL resulted in more in-focus cellular contents such as lobes, cytoplasm, and/or granule. In this example, a PIOAL comprising a viscosity agent (about 30% glycerol) was used to process the sample. The pH was adjusted to a pH of about 6.8 to 7.2 and the sample mixture was made isotonic by (0.9% sodium chloride). The results shown here demonstrate the efficacy of an exemplary PIOAL used on an image analyzer to align cells and intracellular organelles.

FIGS. 4P and 4Q show a comparison of images obtained using a standard sheath fluid (FIG. 4P upper and lower panels) versus images obtained using an exemplary PIOAL fluid (FIG. 4Q upper and lower panels). As shown here, the use of PIOAL resulted in an improved RBC alignment, for example by orienting the major surfaces of the red blood cells to face toward the camera or imaging device. The sample was analyzed using an instrument focusing protocol (on an exemplary target 44 as depicted in FIG. 1) and the target was brought into focus by a visual analyzer. The focusing system was then offset by displacement distance 52, resulting in the particles in the ribbon-shaped sample stream being in focus. The blood sample was previously diluted using a sample diluent. The sample flowed through a cannula and along a flowpath of a flowcell, thereby generating a ribbon-shaped sample stream (e.g. 2 microns in thickness) which was between two layers of PIOAL or standard sheath (in controls). The visual analyzer then generates focused images of the particles in the ribbon-shaped sample stream (e.g. at about 60 frames per second) to be used for analysis. The blood sample is obtained from a subject and processed for analysis by the blood analyzer. Images of RBCs in a flowcell are captured while the sample is processed using a standard sheath fluid or a PIOAL. Relative percentages demonstrate significant improvement in the number of aligned RBCs based on imaging data (e.g. FIGS. 4P and 4Q). The result demonstrated that PIOAL was efficacious at increasing the percentage of RBC alignment while in flow in the ribbon-shaped sample stream using the focusing instrument/protocols as described herein.

It was also observed that the implementation of PIOAL results in improved alignment based on using increasing levels of glycerol (gly) in symmetric and asymmetric flowcells.

Figure 4R:
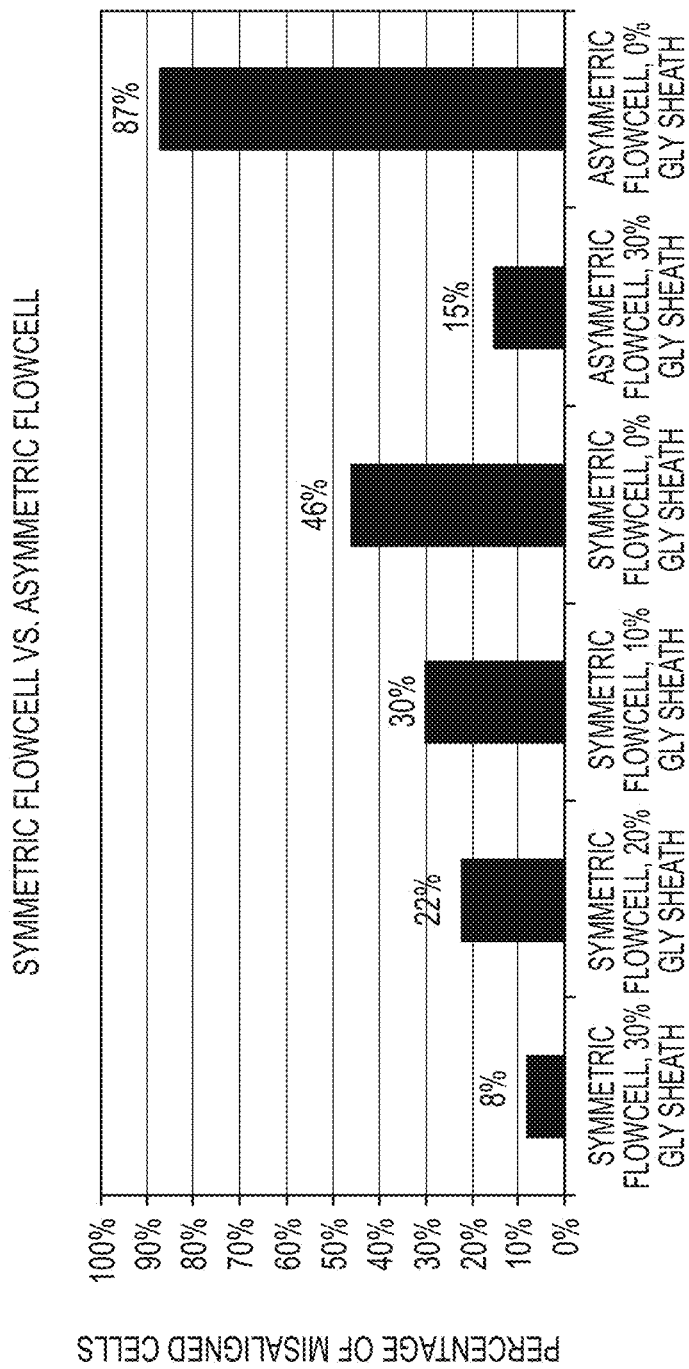
FIG. 4R illustrates certain particle alignment results obtains using flowcell configurations and sheath fluid compositions according to embodiments of the present invention.

The chart in FIG. 4R shows the percentage of non-aligned cells obtained using 0%-30% glycerol in the PIOAL with symmetric vs. asymmetric flow cells. Using 30% glycerol in the PIOAL and a symmetric flowcell results in reducing the percentage of misaligned cells to only 8%. Note without glycerol in the PIOAL, and with an asymmetric cell, the percentage of misaligned cells increased to 87%. Hence, this chart demonstrates the effect of glycerol percentage and flowcell geometry on particle (e.g. RBC) alignment. The addition of glycerol decreases the percentage of misaligned RBC cells using either symmetric or asymmetric flowcell geometry. The % non-aligned RBCs was reduced from 87% down to 15% in the asymmetric and 46% to 8% in symmetrical cells. Thus, the chart provides a comparison between misalignment results (8%) obtained from an analyzer configuration that involves a symmetrical narrowing flowcell transition zone and a viscous sheath fluid and misalignment results (46%) obtained from an analyzer configuration that involves a symmetrical narrowing flowcell transition zone without the use of a viscous sheath fluid.

These results provide evidence for the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties. The PIOAL comprises a diluent and at least one viscosity modifying agent.

Exemplary PIOAL formulation A includes a 30% (v/v) glycerol solution having 300 mL glycerol and QS (quantity sufficient or to bring the final volume up to) to 1 L with diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation B includes a 6.5% (v/v) glycerol solution having 65 mL glycerol and QS to 1 L with suitable exemplary diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation C includes a 5% glycerol (v/v) solution with 1% PVP (w/v) in buffer having 50 mL glycerol, 10 g PVP (MW: 360,000), 1 packet of Sigma PBS powder, at pH 7.4 (0.01M phosphate buffered saline; 0.138M sodium chloride; 0.0027M potassium chloride), and QS to 1 L with deionized water.

Exemplary PIOAL formulation D includes a 1.6% PVP (w/v) solution having 16 g PVP (MW: 360,000) and 1 packet of Sigma PBS powder, at pH 7.4 (0.01M phosphate buffered saline; 0.138M sodium chloride; 0.0027M potassium chloride), and QS to 1 L with deionized water.

FIGS. 5A and 5B depict exemplary flowstream characteristics related to shear force, lateral compression, orientation, differential viscosity, relative movement between sheath and sample fluids, and the like.

Methods

Figure 6:
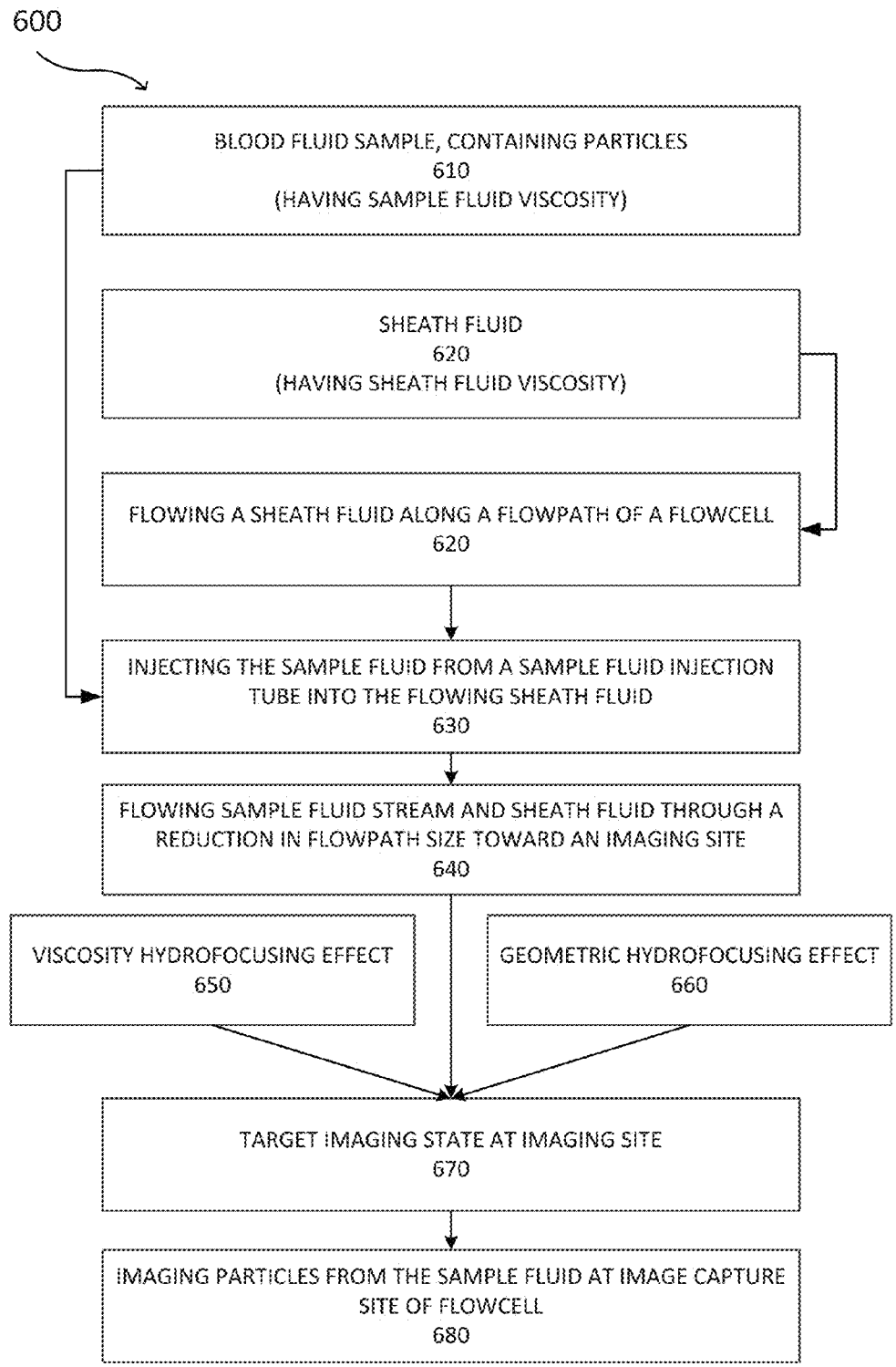
FIG. 6 depicts aspects of particle imaging methods according to embodiments of the present invention.

FIG. 6 depicts aspects of an exemplary method 600 for imaging a plurality of particles using a particle analysis system configured for combined viscosity and geometric hydrofocusing according to embodiments of the present invention. The particles can be included in a blood fluid sample 610 having a sample fluid viscosity. As shown here, the method can include flowing a sheath fluid 620 along a flowpath of a flowcell as indicated by step 630. The sheath fluid 620 can have a sheath fluid viscosity that differs from the sample fluid viscosity by a viscosity difference in a predetermined viscosity difference range. The method can also include injecting the blood fluid sample 610 into the flowing sheath fluid within the flowcell, as indicated by step 630, so as to provide a sample fluid stream enveloped by the sheath fluid. Further, the methods can include flowing the sample fluid stream and the sheath fluid through a reduction in flowpath size toward an imaging site as indicated by step 640. As the sample stream and sheath fluids pass through the reduction in flowpath size or narrowing transition zone, a viscosity hydrofocusing effect induced by an interaction between the sheath fluid and the sample fluid stream associated with the viscosity difference (as depicted in step 650), in combination with a geometric hydrofocusing effect induced by an interaction between the sheath fluid and the sample fluid stream associated with the reduction in flowpath size (as depicted in step 660), is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid as depicted by step 670. Methods may also include imaging the plurality of particles at the imaging site, as depicted by step 680.

Shear Strain Rate

Figure 7:
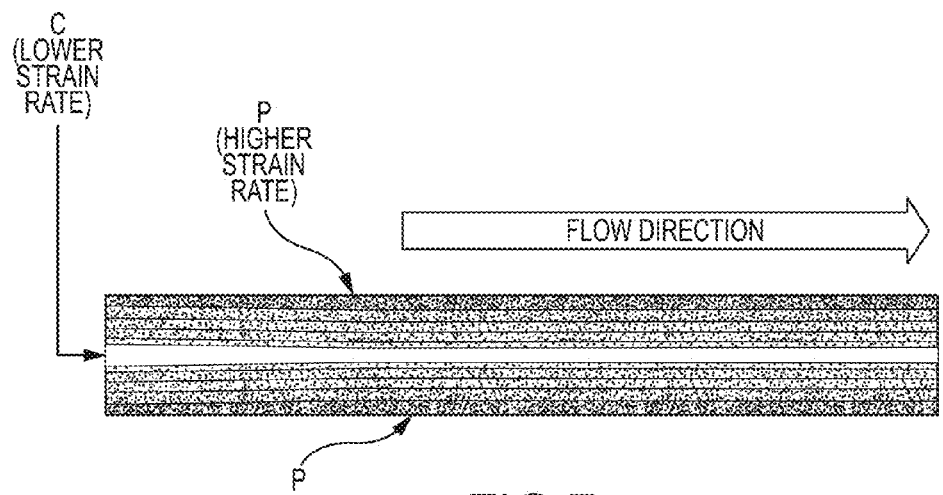
FIGS. 7 and 8 depict aspects of flowstream strain rate according to embodiments of the present invention.
Figure 8:
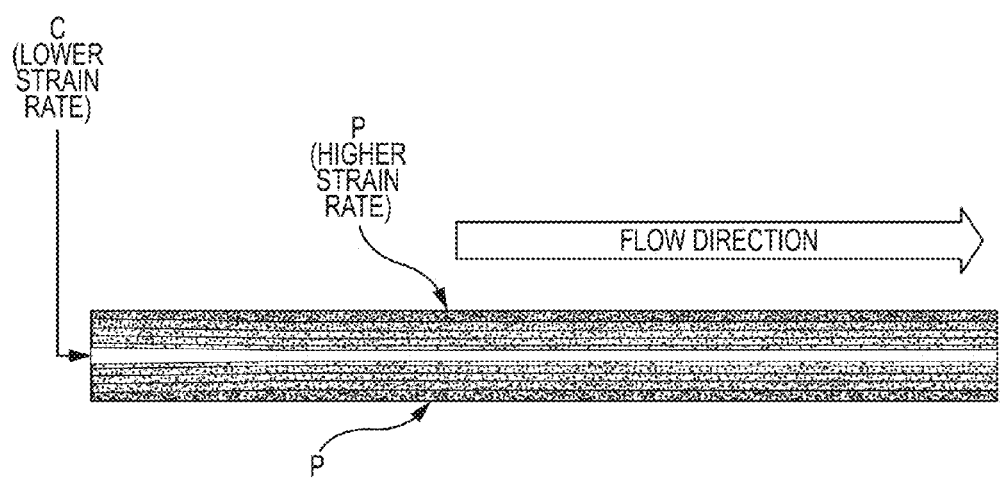

FIGS. 7 and 8 depict aspects of shear strain rate values for certain flow conditions in a flowcell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 7, the sample can have a flow rate of 0.3 µL/sec and the sheath fluid can have a flow rate of 21 µL/sec. With regard to FIG. 8, the sample can have a flow rate of 1 µL/sec and the sheath fluid can have a flow rate of 70 µL/sec. In each of these figures, it can be seen that the flow presents a lower strain value toward the center (C) and a higher strain value toward the periphery (P). Such strain values can correspond to an asymmetric flowcell configuration, in some embodiments.

As depicted in FIG. 7, according to some embodiments, the lower strain rate toward the center (C) portion of the flowstream can have a value of about 500 (1/s) or lower and the higher strain rate toward the periphery (P) of the flowstream can have a value of about 3000 (1/s) or higher. As depicted in FIG. 8, according to some embodiments, the lower strain rate toward the center (C) portion of the flowstream can have a value of about 1000 (1/s) or lower and the higher strain rate toward the periphery (P) of the flowstream can have a value of about 9000 (1/s) or higher.

Hence, it can be seen that lower sample and sheath fluid rates (e.g. FIG. 7) correspond to lower strain rates, and higher sample and sheath fluid rates (e.g. FIG. 8) correspond to higher strain rates. It is understood that embodiments of the present invention encompass the use of sample and/or sheath fluids corresponding to various viscosity values, various strain rate values, and/or various shear stress values.

According to some embodiments, the PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location corresponding to an image capture site. The sample fluid stream may be compressed to approximately 2 to 3 μm in fluid flow thickness. Several blood cell types have diameters larger than the stream thickness. Sheer forces in the direction parallel to the direction of the flow cause an increase of an image projection of the particles under imaging conditions in the focal plane of the high optical resolution imaging device and/or causing the intra-particle structures, for example, intracellular structures, organelles or lobes, to be positioned, repositioned, and/or better-positioned to be substantially parallel to the direction of flow. The high optical resolution imaging device depth of field is up to 7 μm, for example, 1-4 μm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure was based on the surprising and unexpected discovery that the addition of a suitable amount of a viscosity agent in the PIOAL significantly improves particle/cell alignment in a flowcell, leading to a higher percentage of aligned cells, or cellular components in focus, and higher quality images of cells and/or particles in flow. A viscosity differential in combination with a geometric focusing effect of a narrowing transition zone can achieve enhanced alignment and focus results. Improved results can be seen with a velocity differential between the sheath and sample fluid streams. In some cases, improved images with no overlaps of cells and particles are observed when the sample fluid is delivered at a certain rate. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow and to the focal plane FP (e.g. as depicted in FIG. 4K). In some embodiments, a reduction in RBC misalignment and/or increase in RBC alignment is achieved by increasing the viscosity of the PIOAL.

The ribbon-shaped sample stream thickness can be affected by the relative viscosities and flow rates of the sample fluid and the PIOAL. The source of the sample and/or the source of the PIOAL, for example comprising precision displacement pumps, can be configured to provide the sample and/or the PIOAL at controllable flow rates for optimizing the dimensions of the ribbon-shaped sample stream, namely as a thin ribbon at least as wide as the field of view of the high optical resolution imaging device or the digital image capture device.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

The present disclosure provides a technique for automatically achieving a correct working position of the high optical resolution imaging device for focusing on the ribbon-shaped sample stream. The flowcell structure is configured such that the ribbon-shaped sample stream has a fixed and repeatable location between the walls of the flowcell defining the flow path of sample fluid, in a thin ribbon between layers of PIOAL, passing through a viewing zone in the flowcell. In the flowcell embodiments disclosed, for example in FIG. 1-4G, the cross section of the flowpath for the PIOAL can narrow symmetrically at a transition zone, and a sample can be inserted through a flattened orifice such as a tube with a rectangular lumen at the orifice. The narrowing flowpath (for example geometrically narrowing in cross sectional area by a ratio of 20:1 to 40:1) and also due to an optionally greater linear velocity of the PIOAL compared to the flow of the sample, cooperate to flatten the sample cross section by a ratio of about 20:1 to 70:1. According to some embodiments, the ratio can be within a range from 10:1 to 100:1, within a range from 50:1 to 100:1, within a range from 70:1 to 80:1. According to some embodiments, the ratio is 75:1. Effectively, due to the combination of flow rate, viscosity, and geometry, the sample is formed into a thin ribbon. The narrowing flowpath (for example geometrically narrowing in cross sectional area by a ratio of 40:1, or by a ratio between 20:1 to 70:1) and a difference in linear speed of the PIOAL compared to the flow of the sample, cooperate to compress the sample cross section by a ratio of about 20:1 to 70:1. In some embodiments the cross section thickness ratio may be 40:1. In some embodiments the cross section thickness ratio may be 30:1.

As a result, process variations such as the specific linear velocities of the sample and the PIOAL, do not tend to displace the ribbon-shaped sample stream from its location in the flow. Relative to the structure of the flowcell, the ribbon-shaped sample stream location is stable and repeatable.

In another aspect, this invention relates to a kit comprising the particle contrast agent compositions of this invention. The kit may also contain instructions on the use of particle contrast agent composition according to any of the methods described herein. The kit may also include a particle and/or intracellular organelle alignment liquid (PIOAL). The kit may also contain a programmable storage medium and related software for image based identification of particles such as neutrophil, lymphocytes, monocyte, eosinophils, basophils, platelets, reticulocytes, nucleated RBCs, blasts, promyelocytes, myelocytes, metamyelocytes, bacteria, fungi, protists, protozoa, or parasites. The kit may also comprise one or more buffers, which may include isotonic buffers and/or diluents. The kit and or buffer may further comprise a surfactant, a pH adjusting agent, and/or an antimicrobial agent. In other embodiments, the kit may also comprise a cleaning or flushing solution. The kit may also comprise standards for positive and negative controls. In some embodiments the standard may comprise a standard stained cell reagent. The kit may also comprise disposables such as disposable micropipettes, tips or tubes for transferring the components of the kit. The kit may contain any one, or any combination of two or more of these kit components.

The discrimination of blood cells in a blood sample is an exemplary application for which embodiments of the instant invention are particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus, compositions, and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a blood sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. Exemplary autofocus techniques which can be implemented using embodiments of the present invention are disclosed in co-pending U.S. patent application Ser. No. 14/216,811, the content of which is incorporated herein by reference. The flowcell is coupled to a source of sample fluid, such as a diluted and/or treated blood sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

The instant disclosure provides methods and compositions useful for particle and/or intracellular organelle alignment in conducting image-based sample analysis. In some embodiments, this disclosure relates to methods and compositions for combined counting and imaging system with the ability to perform a complete blood count (CBC) and an image based expanded white blood cell (WBC) differential able to identify and count cell types, such as WBCs, RBCs, and/or platelets, including, for example, neutrophils, lymphocytes, monocytes, eosinophils, basophils, reticulocytes, nucleated RBCs, blasts, promyelocytes, myelocytes, or metamyelocytes, and to provide image based information for WBC counts and morphologies, red blood cell (RBC) counts and morphologies and platelet (PLT) counts and morphologies.

In other embodiments, this disclosure relates to a PIOAL that can be used in image based analysis of particles as described herein. Cell category and/or subcategory count in blood samples is used in this disclosure as nonlimiting examples of the sort of samples that may be analyzed. In some embodiments, cells present in samples may also include bacterial or fungal cells as well as white blood cells, red blood cells and/or platelets. In some embodiments, particle suspensions obtained from tissues or aspirates may be analyzed.

In some aspects, samples are presented, imaged and analyzed in an automated manner. In the case of blood samples, the sample may be substantially diluted with a suitable diluent or saline solution, which reduces the extent to which the view of some cells might be hidden by other cells in an undiluted or less-diluted sample. The cells can be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flowcell and imaging.

According to some embodiments, the particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference. According to some embodiments, sample preparation techniques may include staining, lysing, permeabilizing, and other processing modalities such as those described in co-pending U.S. patent application Ser. No. 14/216,339, the content of which is incorporated herein by reference.

The term high optical resolution imaging device can include devices that are capable of obtaining particles images with sufficient visual distinctions to differentiate morphological features and/or changes. Exemplary high optical resolution imaging devices can include devices with an optical resolution of 1 µm or lower, including for example, 0.4 to 0.5 µm, such as for example, 0.46 µm.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

In yet another aspect, the methods of this invention relate to a method for performing image-based red blood cell categorization and subcategorization comprising: a) imaging a portion of the red blood cells; and b) determining the morphology of the imaged red blood cells. As used herein, red blood cells (RBC) can include, for example, normal or abnormal red blood cells, reticulocytes, nucleated red blood cells, and/or malaria-infected cells. In some embodiments, the imaging is performed using the apparatus of this disclosure such as an apparatus comprising a particle counter, a visual analyzer and a processor.

As used herein, an exemplary complete blood count (CBC) can include a test panel typically requested by a doctor or other medical professional that provides information about the particles and/or cells in a patient's blood sample. Exemplary cells that circulate in the bloodstream can be generally divided into three types: including but not limited to, for example, white blood cells (e.g., leukocytes), red blood cells (e.g., erythrocytes), and platelets (e.g., thrombocytes).

As used herein, abnormally high or low counts may indicate the presence of disease, disorder, and/or condition. Thus, a CBC is one of the commonly performed blood tests in medicine, as it can provide an overview of a patient's general health status. Accordingly, a CBC is routinely performed during annual physical examinations.

As used herein, typically a phlebotomist collects the blood sample from the subject, the blood is generally drawn into a test tube typically containing an anticoagulant (e.g., EDTA, sometimes citrate) to stop it from clotting. The sample is then transported to a laboratory. Sometimes the sample is drawn off a finger prick using a Pasteur pipette for immediate processing by an automated counter. In one embodiment, the particle image is acquired while the particle is enveloped in a sheath fluid or PIOAL. In certain embodiments, the blood sample may be viewed on a slide prepared with a sample of the patient's blood under a microscope (a blood film, or peripheral smear). In certain embodiments, the complete blood count is performed by an automated analyzer.

As used herein, data/parameters of a blood count can include, for example, total red blood cells; hemoglobin—the amount of hemoglobin in the blood; hematocrit or packed cell volume (PCV); mean corpuscular volume (MCV)—the average volume of the red cells (anemia is classified as microcytic or macrocytic based on whether this value is above or below the expected normal range. Other conditions that can affect MCV include thalassemia, reticulocytosis and alcoholism); mean corpuscular hemoglobin (MCH)—the average amount of hemoglobin per red blood cell, in picograms; mean corpuscular hemoglobin concentration (MCHC)—the average concentration of hemoglobin in the cells; red blood cell distribution width (RDW)—the variation in cellular volume of the RBC population; total white blood cells; neutrophil granulocytes (may indicate bacterial infection, typically increased in acute viral infections). Due to the segmented appearance of the nucleus, neutrophils are sometimes referred to as "segs." The nucleus of less mature neutrophils is not segmented, but has a band or elongated shape. Less mature neutrophils—those that have recently been released from the bone marrow into the bloodstream—are known as "bands". Other data/parameters for a blood count can also include, for example, lymphocytes (e.g., increased with some viral infections such as glandular fever, and in chronic lymphocytic leukemia (CLL), or decreased by HIV infection); monocytes (may be increased in bacterial infection, tuberculosis, malaria, Rocky Mountain spotted fever, monocytic leukemia, chronic ulcerative colitis and regional enteritis; eosinophil granulocytes (e.g., increased in parasitic infections, asthma, or allergic reaction); basophil granulocytes (e.g., increased in bone marrow related conditions such as leukemia or lymphoma.

As used herein, data/parameters of a blood count can also include, for example, data associated with platelets, including platelet numbers, information about their size and the range of sizes in the blood; mean platelet volume (MPV)—a measurement of the average size of platelets.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

In another aspect of the methods of this invention, the cells are platelets.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

As used herein, detectable and measurable particle parameters can include, for example, visual and/or non-image based indices of size, shape, symmetry, contour and/or other characteristics.

In another embodiment, this disclosure relates to a method for imaging particles using, for example, the kits of this invention, in methods comprising, for example: 1) illuminating the particles with light in a visual analyzer; 2) obtaining a digitized image of sample particles enveloped in a PIOAL; and 3) analyzing particle containing samples based on the image information. In other embodiments, the method may further comprise contacting the sample containing particles with a particle contrast agent composition prior to illuminating the treated sample.

In one embodiment, the particles analyzed comprise at least one of a spherical particle, a non-spherical particle, or both. In another embodiment, the particles comprise at least one spherical particle. In still another embodiment, the particles comprise at least one nonspherical particle. In another embodiment, an image projection of non-spherical particles or particles having non-spherical components is maximized in a plane substantially parallel to the flow direction. The particles may be, for example, WBCs, RBCs, and/or platelets. In one embodiment, at least 50% of the non-spherical particles are aligned in a plane substantially parallel to the direction of flow. In another aspect, use of the PIOALs of this invention in a flowcell permits at least 90% of the non-spherical particles to be aligned in a plane substantially parallel to the direction of flow.

Flow of the cells smaller than the thickness of the ribbon-shaped sample stream enveloped in PIOAL, results in alignment of those cells parallel to the direction of the flow. In one embodiment of this disclosure, at least 92% of the non-spherical particles are aligned in a plane substantially parallel to the direction of flow. In yet another embodiment, at least 90% of the non-spherical particles are aligned a plane substantially parallel to the direction of flow. In another embodiment, at least 75%, 80%, 85%, 86%, 87%, 88%, 89%, 90%, 91%, 92%, 93%, 94% or at least 95% of the particles are substantially aligned, namely within 20 degrees from a plane substantially parallel to the direction of flow. In another embodiment, the percentage of non-spherical and/or spherical particles are aligned in a plane substantially parallel to the direction of flow may be any range between any two of the recited percentages, for example, at least 75-85%, 75-80%, and other ranges such as 75-92%.

Shear forces in the direction parallel to the direction of the flow as a result of flow of larger cells in the sample enveloped in the PIOAL, such as WBCs, results in positioning, repositioning, and/or better positioning of nuclear structures, cytosolic structures or granules or other intracellular components or structures closer to a plane parallel to the direction of the flow In one embodiment, the non-spherical particles comprise red blood cells. In another aspect of this invention, the spherical particles comprise white blood cells or nucleated red blood cells.

In one embodiment of the methods of this invention, the particles are non-spherical particles. In one embodiment, the particles analyzed comprise at least one of a spherical particle, a non-spherical particle, or both. In another embodiment, the particles comprise at least one spherical particle. In still another embodiment, the particles comprise at least one nonspherical particle. In another embodiment, an image projection of non-spherical particles or particles having non-spherical components is maximized in a plane substantially parallel to the direction of flow. The particles may be, for example, RBCs, including reticulocytes and nucleated RBCs, platelets and/or WBC, including a neutrophil, lymphocyte, monocyte, eosinophil, basophil, or immature WBC including a blast, promyelocyte, myelocyte, or metamyelocyte. In one embodiment, at least 50% of the non-spherical particles are aligned in a plane substantially parallel to the direction of flow. In another aspect, use of the PIOALs of this invention in a flowcell permits at least 90% of the non-spherical particles to be aligned in a plane substantially parallel to the direction of flow.

In one embodiment of this disclosure, the image cross-section comprises at least one of differentially stained nuclear structure, differentially stained cytosolic structure or differentially stained granules in a WBC, including a neutrophil, lymphocyte, monocyte, eosinophil, basophil, or immature WBC including a blast, promyelocyte, myelocyte, or metamyelocyte. In another embodiment, at least 50%, 55%, 60%, 65%, 70%, 75%, 80%, 85%, 86%, 87%, 88%, 89%, 90%, 91%, 92%, 93%, 94% or at least 95% of the spherical and/or non-spherical particles have nuclear structures, cytosolic structures or granules in the focal plane or depth of field of the high optical resolution imaging device.

In some embodiments of the methods of this invention, the image information is the image cross-section of a particle. In some aspects, the image cross-section comprises at least one of a differentially stained nuclear structure, a differentially stained cytosolic structure or differentially stained granules in a WBC, including a neutrophil, lymphocyte, monocyte, eosinophil, basophil, or immature WBC including a blast, promyelocyte, myelocyte, or metamyelocyte.

In one embodiment, the methods of this invention provide surprisingly high quality images of cells with a high percentage of particles and particle content in-focus in flow, which are useful in obtaining automated, image based WBC differentials, as well as automated identification of morphological abnormalities useful in determining, diagnosing, prognosing, predicting, or supporting a diagnosis of whether a subject is healthy or has a disease, condition, abnormality or infection and/or is responsive or non-responsive to treatment.

In another aspect, the compositions and methods of this invention provide more accurate image based cell categorization and subcategorization and flagging which greatly reduces the manual review rate compared to current analyzers.

As used herein, exemplary white blood cells (WBC) can include, for example, neutrophils, lymphocytes, monocytes, eosinophils, basophils, immature granulocytes including meta-myelocyes, myelocytes, pro-myelocytes and blasts, and abnormal white blood cells. As used herein, red blood cells (RBC) can include, for example, normal or abnormal red blood cells, reticulocytes, and nucleated red blood cells.

As used herein, viscosity agent can include viscosity agents or viscosity modifiers. An exemplary viscosity agent/modifier has a characteristic viscosity that is different from the viscosity of the sample such that when the PIOAL and the viscosity agent are mixed, the viscosity of the PIOAL is altered or and/or increased in order to maximize the alignment of particles. In certain embodiments, the viscosity difference and/or a speed difference between the ribbon-shaped sample stream and the PIOAL can introduce shear forces to act on the particles while in flow thereby reducing the misalignment and/or causing the particles to align.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

In one embodiment, this disclosure relates to a PIOAL for use in a visual analyzer. In certain embodiments, the PIOAL may comprise at least one of a buffer; a pH adjusting agent; a buffer; a viscosity agent/modifier; ionic strength modifier, a surfactant, a chelating agent, and/or an antimicrobial agent.

In one aspect, the PIOAL may comprise two or more viscosity agents/modifiers.

In one aspect, the PIOAL of this invention may have a viscosity of between about 1 to about 10 centipoise. In one embodiment, the PIOAL of this invention may comprise a viscosity agent/modifier. In one embodiment, the PIOAL comprises up to 100% of a viscosity agent.

As used herein, the viscosity agent and/or viscosity modifier can include any substance suitable to achieve a viscosity of about 1 to about 10 centipoise, with optical characteristics, including optical clarity, appropriate for use in an imaging system. Generally, the viscosity agent or modifier is non-toxic, biocompatible and leaves the cellular structure and contents substantially intact. The viscosity agent and/or viscosity modifier may comprise at least one of glycerol; glycerol derivative; ethylene glycol; propylene glycol (dihydroxypropane); polyethylene glycol; water soluble polymer and/or dextran. In one aspect, the viscosity agent/modifier in the PIOAL may be glycerol. As an example, in one aspect, the viscosity agent/modifier in the PIOAL may be a glycerol derivative. As an example, in one aspect, the viscosity agent/modifier in the PIOAL may be polyvinylpyrrolidone (PVP). As another example, the viscosity agent/modifier in the PIOAL may be ethylene glycol. As another example, the viscosity agent/modifier in the PIOAL may be propylene glycol (dihydroxypropane). As another example, the viscosity agent/modifier in the PIOAL may be polyethylene glycol. As another example, the viscosity agent/modifier in the PIOAL may be water soluble polymer or dextran. In other aspects, the viscosity agent/modifier in the PIOAL may comprise two or more of glycerol, glycerol derivative; ethylene glycol; propylene glycol (dihydroxypropane); polyvinylpyrrolidone (PVP); polyethylene glycol; water soluble polymer or dextran. Viscosity agent/modifying agents may include any agent suitable to provide a viscosity of about 1 to about 10 centipoise, with optical characteristics, including optical clarity, appropriate for use in an imaging system.

As used herein, other exemplary viscosity agents/modifiers can include, for example, natural hydrocolloids (and derivatives), such as Acacia, tragacanth, alginic acid, carrageenan, locust bean gum, guar gum, xanthan gum, gum arabic, guar gum, gelatin, cellulose, alginates, starches, sugars, dextrans; gelatin; sugars (and derivatives), such as dextrose, fructose; polydextrose; dextrans; polydextrans; saccharides; and polysaccharides; semisynthetic hydrocolloids (and derivatives), such as glycerol, methylcellulose, hydroxyethyl starch (hetastarch), sodium carboxymethylcellulose, hydroxyethylcellulose, hydroxypropylmethylcellulose, polyvinylpyrrolidone (PVP); synthetic hydrocolloids (and derivatives), such as Polyvinyl alcohol (PVA) and/or Carbopol®. Other cell compatible viscosity agents/modifiers are also considered useful for this purpose.

In another aspect, the viscosity agent/modifier in the PIOAL may be glycerol present at a concentration of about 1 to about 50% (v/v) of the PIOAL. As an example, in one embodiment, the viscosity agent/modifier may be present in the PIOAL at a concentration of about 5.0% to about 8.0% (v/v). In another aspect, the viscosity agent/modifier may be present at a concentration of about 6.5% (v/v). In one embodiment, the viscosity agent/modifier is glycerol present at a concentration of about 6.5% (v/v).

In yet another embodiment, the PIOAL can comprise a glycerol viscosity agent/modifier present at a concentration of about 30% (v/v).

In another aspect, the viscosity agent/modifier in the PIOAL may be PVP present at a concentration of about 0.5 to about 2.5% (w/v). As an example, in one embodiment, the viscosity agent/modifier PVP may be present in the PIOAL at a concentration of about 1.0 to about 1.6% (w/v). In one embodiment, the PVP is present at a concentration of about 1.0% (w/v).

In another aspect, the viscosity agent/modifier in the PIOAL may be PVP and glycerol. As an example, in one embodiment, the glycerol may be present in the PIOAL at a concentration of about 5% (v/v) in combination with about 1% (w/v) of PVP.

In one embodiment, the PIOAL of this invention may be used in a visual analyzer to image particles. In one aspect, the visual analyzer comprises a flowcell with a symmetrical flow path, and an autofocus component.

A viscosity agent and/or viscosity modifying/adjusting agents, such as glycerol, may be included in the PIOAL. The viscosity agent, or viscosity modifying agent when introduced, can appropriately adjust the viscosity of the PIOAL to the desired range. Any suitable viscosity agent may be used which sufficiently increases the viscosity of the PIOAL, which has suitable optical characteristics to permit high quality imaging of cells in flow. The PIOAL will have a suitable viscosity to align cells and/or cellular structures into a single plane that is substantially parallel to the direction of the flow, thereby, in part, increasing the in-focus contents of the particles.

The PIOAL may be used with any analyzer of this disclosure.

As used herein, the term "glycerols" encompasses glycerol and a derivative of glycerol (hereinafter referred to as glycerol derivative). Examples of a glycerol derivative include thioglycerol, polyglycerol, and the like. Usable examples of polyglycerol may include diglycerol, POLYGLYCERIN #310 (Sakamoto Yakuhin Kogyo Co., Ltd.), POLYGLYCERIN #750 (Sakamoto Yakuhin Kogyo Co., Ltd.), POLYGLYCERIN #500 (Sakamoto Yakuhin Kogyo Co., Ltd.), and the like.

In another embodiment, the PIOAL of this disclosure further comprises a pH adjusting agent. In one aspect, the final pH of the PIOAL and/or the sample is between about 6.0 to about 8.0. In another aspect, the final pH of the PIOAL and/or the sample is between about 6.6 to about 7.4. In one aspect, the final pH of the PIOAL may be the same pH as the prepared sample 12B (referring to FIG. 8).

Exemplary pH adjusting agents can include, for example, acids (exemplars include organic acids and mineral acids), bases (exemplars include organic bases and hydroxides of alkaline metals and alkaline earth metals). Exemplary organic acids can include acetic, lactic, formic, citric, oxalic, and uric acids. Exemplary mineral acids can include, for example, hydrochloric, nitric, phosphoric, sulphuric, boric, hydrofluoric, hydrobromic and perchloric acids. Exemplary organic bases can include, for example, pyridine, methylamine, imidazole, benzimidazole, histidine, phosphazene, and hydroxides of cations. Exemplary hydroxides of alkali metal and alkaline earth metals can include, for example, Potassium hydroxide (KOH), Barium hydroxide ($Ba(OH)_2$), Caesium hydroxide (CsOH), Sodium hydroxide (NaOH), Strontium hydroxide ($Sr(OH)_2$), Calcium hydroxide ($Ca(OH)_2$), Lithium hydroxide (LiOH), and Rubidium hydroxide (RbOH).

In some embodiments, using a buffer, the pH of PIOAL is preferably maintained from about 6.0 to about 8.5, more preferably from about 7.0 to about 8.0. In some embodiments it is preferable to add a buffer agent to the PIOAL in order to adjust the pH of PIOAL. Any suitable buffer agent or agents may be used as long as the agent or agents adjust the pH of the PIOAL to the proper range. Examples of such a buffer agent include PBS, Good's buffers (specifically, tris buffer, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and the like), disodium hydrogenphosphate, sodium dihydrogen phosphate, monobasic potassium phosphate, veronal sodium-HCl, collidine-HCl, tris(hydroxymethyl)aminomethane-maleic acid, tris(hydroxymethyl)aminomethane-HCl, which may be used alone or in combination;.

In another embodiment, the PIOAL of this invention comprises an ionic strength modifier to adjust the ionic strength of the resulting formulation. Exemplary ionic strength modifiers may include $Li^+$, $Na^+$, $K^+$, $Mg^{++}$, $Ca^{++}$, $Cl^-$, $Br^-$, $HCO^-_3$, sulphates, pyrosulphates, phosphates, pyrophosphates (e.g., potassium pyrophosphate), citrates, cacodylates or other suitable salts. In one embodiment, the PIOAL may be isotonic.

Surfactants may be added to the PIOAL. The kinds of surfactants are not particularly limited as long as they are compatible with other components of the PIOAL, and compatible with the ribbon-shaped sample stream and the particles in the sample. Surfactants may include, for example, cationic, anionic, nonionic, and ampholytic surfactants. Exemplary surfactants may include polyoxyethylenealkyl ether-type surfactants, polyoxyethylenealkylphenyl ether-type surfactants, (for example, NISSAN NONION NS-240 (NOF CORPORATION, registered trademark)), polyoxyethylenesorbitan alkyl ester-type surfactants (for example, RHEODOL TW-0120 (Kao Corporation, registered trademark)), polyol copolymers (for example, PLURONIC F-127, F-123, F-109, F-87, F-86, F-68, T-1107, T-1102 (BASF Corporation, registered trademark)), MEGA-8, sucrose monocaprate, deoxy-BIGCHAP, n-octyl-β-D-thioglucoside, n-nonyl-β-D-thiomaltoside, n-heptyl-β-D-thioglucoside, n-octyl-β-D-thioglucoside, CHAPS, CHAPSO, and the like may be used. Other surfactants may include Triton-X-100 and Tween 20 at sample and ribbon-shaped sample stream compatible concentrations.

The concentration of the surfactant in PIOAL is preferably the concentration level at which particles such as cells in the sample are not affected and/or remain substantially intact. Specifically, the concentration is preferably from 5 to 5000 mg/L, more preferably from 100 to 3000 mg/L.

When particles contained in the sample are analyzed with the analyzer, amorphous salts such as ammonium phosphate, magnesium phosphate, calcium carbonate may precipitate in the sample. Chelating agents may be added to the PIOAL in order to dissolve these amorphous salts. The addition of chelating agents enables not only dissolving amorphous salts, but also inhibiting the oxidation of PIOAL. Usable examples of a chelating agent include EDTA salts, CyDTA, DHEG, DPTA-OH, EDDA, EDDP, GEDTA, HDTA, HIDA, Methyl-EDTA, NTA, NTP, NTPO, EDDPO, and the like. The concentration of the chelating agent in the PIOAL is preferable within the range of 0.05 to 5 g/L.

In another embodiment, the PIOAL may further comprise one or more antimicrobial agents. In some aspects, the antimicrobial agent may be, for example, substances which have fungicidal activity (fungicidal agents) and/or substances which have bactericidal activity (bactericidal agents). In certain embodiments, suitable antimicrobial agents can include, for example, parabens, isothiazolinone, phenolics, acidic preservatives, halogenated compounds, quarternia, and alcohol. Exemplary parabens can include Parabens and Paraben salts. Exemplary isothiazolinones can include methylchloroisothiazolinone, methylisothiazolinone, benzisothiazolinone ProClin 150, ProClin 200, ProClin 300, and ProClin 950. Exemplary phenolic types can include phenoxyethanol, benzyl alcohol, and phenethyl alcohol. Exemplary acidic preservatives can include dehydroacetic acid, benzoic acid, sorbic acid, salicylic acid, formic acid, propionic acid. Exemplary halogenated compounds can include 2-bromo-2-nitropropane-1,3-diol, chloroacetamide, chlorobutanol, chloroxylenol, chlorphenesin, dichlorobenzyl alcohol, iodopropynyl butylcarbamate, methyldibromo glutaronitrile. Exemplary quaternia can include benzalkonium chloride, benzethonium chloride, chlorhexidine, hexamidine diisethionate, and polyaminopropyl biguanide. Exemplary alcohols can include ethyl alcohol and isopropyl alcohol. Examples thereof include triazine antimicrobial agents, thiazole bactericidal agents (for example, benzisothiazolone etc.), pyrithione, pyridine bactericidal agents (for example, 1-hydroxy pyridine-2-thiosodium etc.), 2-phenoxyethanol, and the like. Specifically, Proxel GXL (Avecia), TOMICIDE S (API Corporation), and the like may be used. The bactericidal and/or fungicidal agents help improve the stability of the PIOAL.

In one embodiment, the concentration of the antimicrobial agent may be 0.01% to 0.5% (w/v). The concentration may be 0.03 to 0.05% (w/v).

The sample which is subjected to analysis using the analyzer with the PIOAL in the embodiment is not particularly limited. Samples obtained from the living body (biological samples) are normally used. Alternatively, those samples can be diluted, purified, contacted with a contrast agent, or the like for use. Specifically, examples of such a sample may include blood, semen, cerebrospinal fluid, and the like. Samples may also include particle suspensions derived from tissue samples. The PIOAL in the embodiment is suitably used when particles (red blood cell, white blood cell, bacteria, etc.) are analyzed.

The PIOAL of this invention may be used in a visual analyzer that images particles. In one aspect, the visual analyzer comprises a flowcell capable of maintaining the flow of a ribbon-shaped sample stream with predetermined dimensional characteristics, such as an advantageous ribbon-shaped sample stream thickness. In some embodiments, the flowcell may have a symmetrical flow path, and be used in combination with an autofocus component.

This disclosure relates to a method for imaging a particle comprising: 1) contacting the sample with a particle contrast agent composition; 2) illuminating the prepared particle; 3) obtaining a digitized image of the particle in a ribbon-shaped sample stream enveloped in a PIOAL; and; 4) analyzing the image information to categorize or subcategorize the particles. In some embodiments, the particle may be at least one of, a WBC, RBC, and/or platelet, including, for example, a neutrophil, lymphocyte, monocyte, eosinophil, basophil, reticulocyte, nucleated RBC, blast, promyelocyte, myelocyte, or metamyelocyte, cell, bacteria, parasites, particulate matter, cell clump, cellular component, and immature granulocyte. In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed based on particle image information.

In some embodiments the visual analyzer comprises a flowcell with a symmetrical or an asymmetrical flowpath, and an autofocus component.

In a general aspect, the exemplary PIOAL and methods of use thereof are useful when employed in combination with an automated analyzer found in research and/or medical laboratories. Exemplary automated analyzers are instrument designed to measure different formed elements and/or other characteristics in a number of biological samples, quickly, including, for example, human body fluid samples, with minimal human assistance. Exemplary automated analyzers can include, for example, hematology analyzers and/or cell counters, which can perform for example, complete blood count (CBC) determination. The exemplary analyzers can process samples singly, in batches, or continuously.

In one aspect, the exemplary analyzer/system comprises an automated particle counter configured to detect a plurality of particles that meet one or more selection criteria, and to provide a particle count thereof, wherein the selection criteria encompasses members of at least two categories within said particles. An analyzer, which may comprise a processor, which may include components of the counter, is programmed to distinguish the particles of the at least two categories. A distribution of each of the particles is determined using the analyzer. The processor uses the distribution to correct the particle count for the members of at least one of the at least two categories and/or subcategories. In some embodiments, the particle counter comprises at least one channel configured to provide the particle count of the at least one category and/or subcategory of particles based on a predetermined range based on volume, size, shape, and/or other criterion. For example, the members of the at least one category and/or subcategory comprise at least one type of particle selected from a group consisting of subcategories of white blood cells (WBCs), red blood cells (RBCs), giant platelets (PLTs), and nucleated red blood cells (NRBCs). On a particle counter, due to similar size or other measured characteristic, cells such as giant PLTs and NRBC's may be counted as WBCs. By operating the apparatus as described herein, particle count or concentration of giant PLTs and NRBC's can be measured accurately.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A method for imaging a plurality of particles using a particle analysis system configured for combined viscosity and geometric hydrofocusing, the particles included in a blood fluid sample having a sample fluid viscosity, the method comprising:

flowing a sheath fluid along a flowpath of a flowcell, the sheath fluid having a sheath fluid viscosity that differs from the sample fluid viscosity by a viscosity difference in a predetermined viscosity difference range;

injecting the blood fluid sample into the flowing sheath fluid within the flowcell so as to provide a sample fluid stream enveloped by the sheath fluid;

flowing the sample fluid stream and the sheath fluid through a reduction in flowpath size toward an imaging site, such that a viscosity hydrofocusing effect induced by an interaction between the sheath fluid and the sample fluid stream associated with the viscosity difference, in combination with a geometric hydrofocusing effect induced by an interaction between the sheath fluid and the sample fluid stream associated with the reduction in flowpath size, is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid; and imaging the plurality of particles at the imaging site.

2. The method of claim 1, wherein the target imaging state comprises a target orientation of one or more target particles in the flow relative to a focal plane of an imaging device used to acquire images at the imaging site.

3. The method of claim 1, wherein the plurality of particles comprise a member selected from the group consisting of a red blood cell, a white blood cell, and a platelet.

4. The method of claim 1, wherein the plurality of particles include a cell having an intraparticle structure comprising a member selected from the group consisting of an intracellular structure, an organelle, and a lobe.

5. The method of claim 1, wherein the sheath fluid has a viscosity between 1-10 centipoise (cP).

6. The method of claim 1, wherein the predetermined viscosity difference has an absolute value within a range from about 0.1 to about 10 centipoise (cP).

7. The method of claim 1, wherein the viscosity agent of the sheath fluid comprises a member selected from the group consisting of glycerol, glycerol derivative, ethylene glycol, propylene glycol (dihydroxypropane), polyethylene glycol, polyvinylpyrrolidone (PVP), carboxymethylcellulose (CMC), water soluble polymer(s) and dextran.

8. The method of claim 1, wherein the viscosity agent of the sheath fluid comprises glycerol at a concentration between about 1 to about 50% (v/v).

9. The method of claim 1, wherein the viscosity agent of the sheath fluid comprises glycerol and polyvinylpyrrolidone (PVP).

10. The method of claim 1, wherein the viscosity agent of the sheath fluid comprises glycerol at a concentration of 5% (v/v) and glycerol and polyvinylpyrrolidone (PVP) at a concentration of 1% (v/v).

11. The method of claim 1, wherein the plurality of particles comprise a set of non-spherical particles, the blood fluid sample has a direction of flow at the imaging site, and at least 90% of the set of non-spherical particles are aligned within 20 degrees from a plane substantially parallel to the direction of flow.

12. A system for imaging a plurality of particles in a blood fluid sample having a sample fluid viscosity, the system for use with a sheath fluid having a sheath fluid viscosity that differs from the sample fluid viscosity by a viscosity difference in a predetermined viscosity difference range, the system comprising:

a flowcell having a flowpath and a sample fluid injection tube, the flowpath having a reduction in flowpath size;

a sheath fluid input in fluid communication with the flowpath of the flowcell so as to transmit a flow of the sheath fluid along the flowpath of the flowcell;

a blood fluid sample input in fluid communication with the injection tube of the flowcell so as to inject a flow of the blood fluid sample into the flowing sheath fluid within the flowcell, such that as the sheath fluid and the sample fluid flow through the reduction in flowpath size and toward an imaging site, a viscosity hydrofocusing effect induced by an interaction between the sheath fluid and the sample fluid associated with the viscosity difference, in combination with a geometric hydrofocusing effect induced by an interaction between the sheath fluid and the sample fluid associated with the reduction in flowpath size, provides a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid; and an imaging device that images the plurality of particles at the imaging site.

13. The system of claim 12, wherein the target imaging state comprises a target orientation of one or more target particles in the flow relative to a focal plane of an imaging device used to acquire images at the imaging site.

14. The system of claim 12, wherein the plurality of particles comprise a member selected from the group consisting of a red blood cell, a white blood cell, and a platelet.

15. The system of claim 12, wherein the plurality of particles include a cell having an intraparticle structure comprising a member selected from the group consisting of an intracellular structure, an organelle, and a lobe.

16. The system of claim 12, wherein the predetermined viscosity difference has an absolute value within a range from about 0.1 to about 10 centipoise (cP).

17. The system of claim 12, wherein the viscosity agent of the sheath fluid comprises a member selected from the group consisting of glycerol, glycerol derivative, ethylene glycol, propylene glycol (dihydroxypropane), polyethylene glycol, polyvinylpyrrolidone (PVP), carboxymethylcellulose (CMC), water soluble polymer(s) and dextran.

18. The system of claim 12, wherein the viscosity agent of the sheath fluid comprises glycerol at a concentration between about 1 to about 50% (v/v).

19. The system of claim 12, wherein the viscosity agent of the sheath fluid comprises glycerol and polyvinylpyrrolidone (PVP).

20. The system of claim 12, wherein the viscosity agent of the sheath fluid comprises glycerol at a concentration of 5% (v/v) and glycerol and polyvinylpyrrolidone (PVP) at a concentration of 1% (w/v).

21. The system of claim 12, wherein the plurality of particles comprise a set of non-spherical particles, the blood fluid sample has a direction of flow at the imaging site, and at least 90% of the set of non-spherical particles are aligned within 20 degrees from a plane substantially parallel to the direction of flow.

* * * * *